United States Patent
Addison et al.

(10) Patent No.: US 10,674,964 B2
(45) Date of Patent: Jun. 9, 2020

(54) DETERMINING CHANGES TO AUTOREGULATION

(71) Applicant: Covidien LP, Mansfield, MA (US)

(72) Inventors: Paul S. Addison, Edinburgh (GB); Dean Montgomery, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 141 days.

(21) Appl. No.: 15/962,468

(22) Filed: Apr. 25, 2018

(65) Prior Publication Data
US 2019/0328334 A1 Oct. 31, 2019

(51) Int. Cl.
*A61B 5/00* (2006.01)
*A61B 5/0205* (2006.01)
(Continued)

(52) U.S. Cl.
CPC .......... *A61B 5/7246* (2013.01); *A61B 5/0205* (2013.01); *A61B 5/7278* (2013.01);
(Continued)

(58) Field of Classification Search
CPC ..... A61B 5/7246; A61B 5/0205; A61B 5/742; A61B 5/7278; A61B 5/0295; A61B 5/021; A61B 5/14552; G16H 20/30
See application file for complete search history.

(56) References Cited

U.S. PATENT DOCUMENTS 4,688,577 A 8/1987 Bro
5,579,774 A 12/1996 Miller et al.
(Continued)

FOREIGN PATENT DOCUMENTS

CN 100399990 A 12/2006
DE 10331027 A1 1/2005
(Continued)

OTHER PUBLICATIONS

Ameloot et al., "An observational near-infrared spectroscopy study on cerebral autoregulation in post-cardiac arrest patients: Time to drop 'one-size-fits-all' hemodynamic targets?," Resuscitation 90, 121-126, Jan. 2015.
(Continued)

*Primary Examiner* — Catherine M Voorhees
*Assistant Examiner* — Roland Dinga
(74) *Attorney, Agent, or Firm* — Shumaker & Sieffert, P.A.

(57) ABSTRACT

In some examples, a device includes processing circuitry configured to determine a set of correlation coefficient values for first and second physiological parameters. The processing circuitry is further configured to determine a metric of the correlation coefficient values for a first plurality of bins and for a second plurality of bins, wherein each bin of the first plurality has a first bin parameter and each bin of the second plurality of bins has a second bin parameter different than the first bin parameter. The processing circuitry is also configured to determine a composite estimate of a limit of autoregulation of the patient based on the metric for the first plurality of bins and the metric for the second plurality of bins. The processing circuitry is configured to determine an autoregulation status based on the composite estimate and output, for display via the display, an indication of the autoregulation status.

20 Claims, 9 Drawing Sheets

(51) Int. Cl.
*G16H 20/30* (2018.01)
*A61B 5/1455* (2006.01)
*A61B 5/021* (2006.01)
*A61B 5/0295* (2006.01)

(52) U.S. Cl.
CPC ............. *A61B 5/742* (2013.01); *G16H 20/30* (2018.01); *A61B 5/021* (2013.01); *A61B 5/0295* (2013.01); *A61B 5/14552* (2013.01)

(56) References Cited

U.S. PATENT DOCUMENTS

| | | |
|---|---|---|
| 6,438,399 B1 | 8/2002 | Kurth |
| 6,599,251 B2 | 7/2003 | Chen et al. |
| 6,875,176 B2 | 4/2005 | Mourad et al. |
| 7,532,919 B2 | 5/2009 | Soyemi et al. |
| 7,744,541 B2 | 6/2010 | Baruch et al. |
| 7,998,075 B2 | 8/2011 | Ragauskas et al. |
| 8,057,398 B2 | 11/2011 | Mcnames et al. |
| 8,062,224 B2 | 11/2011 | Ragauskas et al. |
| 8,211,022 B2 | 7/2012 | Lo et al. |
| 8,366,627 B2 | 2/2013 | Kashif et al. |
| 8,433,384 B2 | 4/2013 | Bechtel et al. |
| 8,512,260 B2 | 8/2013 | Grudic et al. |
| 8,556,811 B2 | 10/2013 | Brady |
| 8,852,094 B2 | 10/2014 | Al-ali et al. |
| 9,192,330 B2 | 11/2015 | Lin et al. |
| 9,861,317 B2 | 1/2018 | Ochs |
| 2002/0099295 A1 | 7/2002 | Gil et al. |
| 2003/0219797 A1 | 11/2003 | Zhao et al. |
| 2009/0326386 A1 | 12/2009 | Sethi et al. |
| 2010/0030054 A1 | 2/2010 | Baruch et al. |
| 2011/0105912 A1 | 5/2011 | Widman et al. |
| 2011/0201962 A1* | 8/2011 | Grudic ................... A61B 5/021 600/561 |
| 2012/0004517 A1 | 1/2012 | Starr et al. |
| 2012/0253211 A1 | 10/2012 | Brady et al. |
| 2013/0144140 A1 | 6/2013 | Frederick et al. |
| 2013/0190632 A1 | 7/2013 | Baruch et al. |
| 2014/0073888 A1 | 3/2014 | Kim |
| 2014/0278285 A1 | 9/2014 | Marmarelis et al. |
| 2015/0230758 A1 | 8/2015 | Ochs |
| 2016/0081563 A1 | 3/2016 | Wiard et al. |
| 2016/0106372 A1* | 4/2016 | Addison ............... A61B 5/7221 600/324 |
| 2016/0162786 A1 | 6/2016 | Grudic et al. |
| 2016/0220115 A1 | 8/2016 | Fisher et al. |
| 2016/0324425 A1 | 11/2016 | Addison et al. |
| 2016/0345913 A1* | 12/2016 | Montgomery ....... A61B 5/7275 |
| 2016/0367197 A1* | 12/2016 | Addison ............ A61B 5/02028 |
| 2017/0105631 A1 | 4/2017 | Addison et al. |
| 2018/0014791 A1 | 1/2018 | Montgomery et al. |
| 2018/0338731 A1* | 11/2018 | Addison ................ G16H 50/20 |

FOREIGN PATENT DOCUMENTS

| | | |
|---|---|---|
| RU | 2465829 C1 | 11/2012 |
| WO | WO 2016015057 A1 | 1/2016 |

OTHER PUBLICATIONS

Brady, MD, et al., "Monitoring Cerebrovascular Autoregulation Refining care goals in the ICU," Apr. 21, 2009, 15 pp.

Brady, MD et al., "Real-time continuous monitoring of cerebral blood flow autoregulation using near-infrared spectroscopy in patients undergoing cardiopulmonary bypass," Stroke 41, pp. 1951-1956, Feb. 2010.

Brady, MD et al., "A Dynamic Association Between Cavopulmonary Shunt Pressure and Cerebrovascular Autoregulation in an Infant With Congenital Heart Disease and Intracranial Hemorrhage," J. Cardiothorac. Vasc. Anesth. Vo. 23, No. 2, pp. 215-218; Apr. 2009.

Brady, MD et al., "Continuous Measurement of Autoregulation by Spontaneous Fluctuations in Cerebral Perfusion Pressure: Comparison of 3 Methods," Stroke. 39, pp. 2531-2537; Sep. 2008.

Brady, MD et al., "Continuous Monitoring of Cerebrovascular Pressure Reactivity After Traumatic Brain Injury in Children," Pediatrics 124, e1205-e1212, Dec. 2009.

Brady, MD et al., "Continuous Time-Domain Analysis of Cerebrovascular Autoregulation Using Near-infrared Spectroscopy," Stroke 38, pp. 2818-2825; Oct. 2007.

Brady, MD et al., "Monitoring Cerebral Blood Flow Pressure Autoregulation in Pediatric Patients During Cardiac Surgery," Stroke 41, 1957-1962, Sep. 2010.

Brady, MD et al., "Noninvasive Autoregulation Monitoring With and Without Intracranial Pressure in the Naïve Piglet Brain," Anesth. Analg. vol. 111, No. 1, 191-195; Jul. 2010.

Budohoski, MD et al., "Bilateral Failure of Cerebral Autoregulation is Related to Unfavorable Outcome After Subarachnoid Hemorrhage," Neurocrit. Care 22, 65-73, Jul. 2014.

Budohoski, MD, et al., "The Relationship Between Cerebral Blood Flow Autoregulation and Cerebrovascular Pressure Reactivity After Traumatic Brain Injury," Neurosurgery 71, pp. 652-660 May 2012.

Calviere et al., "Prediction of Delayed Cerebral Ischemia After Subarachnoid Hemorrhage Using Cerebral Blood Flow Velocities and Cerebral Autoregulation Assessment," Neurocrit. Care, Feb. 2015.

Czosnyka, PhD, et al., "Intracranial pressure: More Than a Number," Neurosurg. Focus 22, E10, May 2007.

Czosnyka, PhD, et al., "Monitoring of Cerebrovascular Autoregulation: Facts, myths, and missing links," Neurocrit. Care 10, 373-386, Jan. 2009.

Czosnyka, PhD, et al., "Monitoring of Cerebral Autoregulation in Head-Injured Patients," Stroke. 27, 1829-1834, Oct. 1996.

Depreitere et al., "Pressure autoregulation monitoring and cerebral perfusion pressure target recommendation in patients with severe traumatic brain injury based on minute-by-minute monitoring data," J. Neurosurg. 120, pp. 1451-1457, Apr. 2014.

Dias et al., "Kidney-Brain Link in Traumatic Brain Injury Patients? A preliminary report," Neurocrit. Care, Oct. 2014, 12 pp.

Dias et al., "Optimal Cerebral Perfusion Pressure Management at Bedside: A Single-Center Pilot Center Pilot Study," Neurocrit. Care, Jan. 2015, 13 pp.

Diedler, MD et al., "The Limitations of Near-Infrared Spectroscopy to Assess CerebrovascularR: The Role of Slow Frequency Oscillations," Anesth. Analg. vol. 113 No. 4, pp. 849-857, Oct. 2011.

Donnelly et al., "Further understanding of cerebral autoregulation at the bedside: possible implications for future therapy," Expert Rev. Neurother. 15, pp. 169-185, Jan. 2015.

Eide, MD, PhD., et al. "Pressure-derived versus pressure wave amplitude—derived indices of cerebrovascular pressure reactivity in relation to early clinical state and 12-month outcome following aneurysmal subarachnoid hemorrhage," J. Neurosurg. 116, pp. 961-971, May 2012.

Gilmore et al., "Relationship between cerebrovascular dysautoregulation and arterial blood pressure in the premature infant," J. Perinatol. 31, pp. 722-729, Mar. 2011.

Hori et al., "Effect of carotid revascularization on cerebral autoregulation in combined cardiac surgery," Eur. J. Cardio-Thoracic Surg., Feb. 2015, 7 pp.

Howells et al., "An optimal frequency range for assessing the pressure reactivity index in patients with traumatic brain injury," J. Clin. Monit. Comput., pp. 97-105, Mar. 2014.

Howlett et al., "Cerebrovascular autoregulation and neurologic injury in neonatal hypoxic-ischemic encephalopathy," Pediatr. Res. vol. 74, No. 5, pp. 525-535, Nov. 2013.

Jaeger, MD et al., "Effects of cerebrovascular pressure reactivity-guided optimization of cerebral perfusion pressure on brain tissue oxygenation after traumatic brain injury," Crit. Care Med. vol. 38, No. 5, pp. 1343-1347, May 2010.

Jaeger, MD, et al., "Continuous monitoring of cerebrovascular autoregulation after subarachnoid hemorrhage by brain tissue oxygen pressure reactivity and its relation to delayed cerebral infarction," Stroke 38, pp. 981-986, Apr.-May 2007.

Kvandal et al., "Impaired cerebrovascular reactivity after acute traumatic brain injury can be detected by wavelet phase coherence analysis of the intracranial and arterial blood pressure signals," J. Clin. Monit. Comput. 27, pp. 375-383, May 2013.

(56) References Cited

OTHER PUBLICATIONS

Laflam et al., "Shoulder Surgery in the Beach Chair Position Is Associated with Diminished Cerebral Autoregulation but No Differences in Postoperative Cognition or Brain Injury Biomarker Levels Compared with Supine Positioning," Anesth. Analg. vol. 120, No. 1, pp. 176-185, Jan. 2015.

Lang MD, PhD, et al., "A Review of Cerebral Autoregulation: Assessment and Measurements," Aust. Anaesth. 161-172, 2005, (Applicant points out, in accordance with MPEP 609.04(a), that the year of publication, 2005, is sufficiently earlier than the effective U.S. filing date, Mar. 5, 2018, so that the particular month of publication is not in issue.).

Lang et al., "Short pressure reactivity index versus long pressure reactivity index in the management of traumatic brain injury," J. Neurosurg. vol. 122, pp. 588-594, Mar. 2015.

Lang et al., "Continuous monitoring of cerebrovascular autoregulation: a validation study," J. Neurol. Neurosurg. Psychiatry 72, pp. 583-586, Jan. 2002.

Lee et al., "A pilot study of cerebrovascular reactivity autoregulation after pediatric cardiac arrest," Resuscitation 85, pp. 1387-1393, Jun. 2014.

Lee, J. K. et al., "Cerebral blood flow and cerebrovascular autoregulation in a swine model of pediatric cardiac arrest and hypothermia*," Crit. Care Med. vol. 39, No. 10, pp. 2337-2345, Oct. 2011.

Lee, MD et al., "Cerebrovascular Reactivity Measured by Near-Infrared Spectroscopy," Stroke 40, pp. 1820-1826, Oct. 2009.

Lee, MD, et al., "Noninvasive autoregulation monitoring in a swine model of pediatric cardiac arrest," Anesth. Analg. vol. 114, pp. 825-836, Apr. 2012.

Lewis et al., "Continuous Correlation Between Intracranial Pressure and Cerebral Blood Flow Velocity Reflects Cerebral Autoregulation Impairment During Intracranial Pressure Plateau Waves," Neurocrit. Care 21, pp. 514-525, May 2014.

Liu et al., "Comparison of frequency and time domain methods of assessment of cerebral autoregulation in traumatic brain injury," J. Cereb. Blood Flow Metab. 35, pp. 248-256, Nov. 2014.

Nasr et al., "Baroreflex and Cerebral Autoregulation Are Inversely Correlated," Circ. J. vol. 78, pp. 2460-2467, Oct. 2014.

Nasr et al., "Cerebral autoregulation in patients with obstructive sleep apnea syndrome during wakefulness," Eur. J. Neurol. 16, pp. 386-391, Mar. 2009.

Ono, MD et al., "Blood pressure excursions below the cerebral autoregulation threshold during cardiac surgery are associated with acute kidney injury," Crit. Care Med. 41, pp. 464-471, Feb. 2013.

Ono, MD et al., "Cerebral Blood Flow Autoregulation Is Preserved After Hypothermic Circulatory Arrest," Ann. Thorac. Surg. 96, pp. 2045-2053, Dec. 2013.

Ono, MD et al., "Duration and magnitude of blood pressure below cerebral autoregulation threshold during cardiopulmonary bypass is associated with major morbidity and operative mortality," J. Thorac. Cardiovasc. Surg. 147, pp. 483-489, Jan. 2014.

Ono, MD et al., "Risks for impaired cerebral autoregulation during cardiopulmonary bypass and postoperative stroke," Br. J. Anaesth. 109, pp. 391-398, Jun. 2012.

Ono, MD et al., "Validation of a Stand-Alone Near-Infrared Spectroscopy System for Monitoring Cerebral Autoregulation During Cardiac Surgery," Anesth. Analg. vol. 116, No. 1, pp. 198-204, Jan. 2013.

Papademetriou et al., "Multichannel near infrared spectroscopy indicates regional variations in autoregulation in infants supported on extracorporeal membrane oxygenation," J. Biomed. Opt., vol. 17, pp. 067008-1-067008-9, Jun. 2012.

Radolovich et al., "Pulsatile Intracranial Pressure and Cerebral Autoregulation After Traumatic Brain Injury," Neurocrit. Care 15, pp. 379-386, Dec. 2011.

Radolovich et al., "Reactivity of Brain Tissue Oxygen to Change in Cerebral Perfusion Pressure in Head Injured Patients, " Neurocrit. Care 10, pp. 274-279, Feb. 2009.

Reinhard, MD et al., "Cerebral Autoregulation in Carotid Artery Occlusive Disease Assessed From Spontaneous Blood Pressure Fluctuations by the Correlation Coefficient Index," Stroke 34, pp. 2138-2144, May 2003.

Reinhard, MD et al., "Cerebral dysautoregulation and the risk of ischemic events in occlusive carotid artery disease," J. Neurol. 255, pp. 1182-1189, Jun. 2008.

Schmidt et al., "Impaired autoregulation is associated with mortality in severe cerebral diseases" Clinical Neurosciences and Mental Health, 1 (Suppl. 1), May 2014, 6 pp.

Schmidt et al., "Asymmetry of cerebral autoregulation does not correspond to asymmetry of cerebrovascular pressure reactivity," Perspect. Med. 1-12, pp. 285-289, Sep. 2012.

Schmidt et al., "Cerebral Autoregulatory Response Depends on the Direction of Change in Perfusion Pressure," J. Neurotrauma 26, pp. 651-656, May 2009.

Severdija et al., "Assessment of dynamic cerebral autoregulation and cerebral carbon dioxide reactivity during normothermic cardiopulmonary bypass," Med. Biol. Eng. Comput. 53, pp. 195-203, Nov. 2014.

Smith, "Shedding light on the adult brain: a review of the clinical applications of near-infrared spectroscopy," Philos. Trans. R. Soc. A Math. Phys. Eng. Sci. 369, pp. 4452-4469 Oct. 2011.

Soul et al., "Fluctuating Pressure-Passivity Is Common in the Cerebral Circulation of Sick Premature Infants," Pediatric Research 61, No. 4, Nov. 2007, pp. 467-473.

Steiner, MD et al., "Continuous monitoring of cerebrovascular pressure reactivity allows determination of optimal cerebral perfusion pressure in patients with traumatic brain injury," Crit. Care Med. 30, pp. 733-738, Apr. 2002.

Steiner et al., "Near-Infrared Spectroscopy Can Monitor Dynamic Cerebral Autoregulation in Adults," Neurocrit. Care 10, pp. 122-128, Sep. 2008.

Tekes et al., "Apparent Diffusion Coefficient Scalars Correlate with Near-Infrared Spectroscopy Markers of Cerebrovascular Autoregulation in Neonates Cooled for Perinatal Hypoxic-Ischemic Injury," Am. J. Neuroradiol. 36, pp. 188-193, Jan. 2015.

Zheng et al., "Continuous Cerebral Blood Flow Autoregulation Monitoring in Patients Undergoing Liver Transplantation," Neurocrit. Care 17, pp. 77-84, Aug. 2012.

Zweifel et al., "Continuous Assessment of Cerebral Autoregulation With Near-Infrared Spectroscopy in Adults After Subarachnoid Hemorrhage," Stroke 41, pp. 1963-1968, Jan. 2010.

Zweifel et al., "Continuous time-domain monitoring of cerebral autoregulation in neurocritical care," Med. Eng. Phys. 36, 638-645, Feb. 2014.

Tsalach et al., "Cerebral Autoregulation Real-Time Monitoring," PLOS One, Aug. 29, 2016, 14 pp.

Chung MD, PhD et al., "Assessment of Noninvasive Regional Brain Oximetry in Posterior Reversible Encephalopahty Syndrome and Reversible Cerebral Vasoconstriction Syndrome," Journal of Intensive Care Medicine, vol. 31(6), Jan. 2016, pp. 415-419.

Lee et al., "Cerebrovascular Autoregulation in pediatric moyamoya Disease" Pediatric Anesthesia, 23, pp. 547-556, Jun. 2013.

Steppan, MD, et al., "Cerebral and Tissue Oximetryc" Best Pract Res Clin Anaesthesiol, Dec. 2014, pp. 429-439.

Brady et al., "A New Monitor of Pressure Autoregulation: What Does It Add?" International Anesthesia Research Society, Nov. 2015, vol. 121, No. 5, pp. 1121-1123.

Prabhakar et al., "Current concepts of optimal cerebral perfusion pressure in traumatic brain injury," J. Anaesthesiol Clin Pharmacol, Jul.-Sep. 2014, pp. 318-327.

Lang et al., "Continuous monitoring of cerebrovascular autoregulation: a validation study," J Neurol Neurosurg Psychiatry, pp. 583-586, Jan. 2002.

Lazaridis et al., Optimal cerebral perfusion pressure: are we ready for it? Neurological Research, vol. 35, No. 2, Nov. 12, 2013, pp. 138-148.

Joshi et al., "Predicting the Limits of Cerebral Autoregulation During Cardiopulmonary Bypass," Anesthesia-Analgesia, Mar. 2012, vol. 114, No. 3, pp. 503-510.

(56) References Cited

OTHER PUBLICATIONS

Olsen et al., "Validation of Transcranial Near-Infrared Spectroscopy for Evaluation of Cerebral Blood Flow Autoregulation," Journal of Neurosurgical Anesthesiology, pp. 280-285, Oct. 1996.

Addison et al., "Gradient adjustment method for better discriminating correlating and non-correlating regions of physiological signals: application to the partitioning of impaired and intact zones of cerebral autoregulation," J Clin Moit Comput, Aug. 2016, 11 pp.

Montgomery et al., "Data clustering methods for the determination of cerebral autoregulation functionality," J Clin Monit Comput, Sep. 2015, 8 pp.

Brady et al., "The Lower Limit of Cerebral Blood Flow Autoregulation is Increased with Elevated Intracranial Pressure," vol. 108, No. 4, Apr. 2009.

Gao et al., "Mathematical considerations for modeling cerebral blood flow autoregulation to systemic arterial pressure," accessed on Sep. 19, 2016, accessed from http://ajpheart.physiology.org/., pp. H1023-H1031.

Hauerberg et al., "The Upper Limit of Cerebral Blood Flow Autoregulation in Acute Intracranial Hypertension," Journal of Neurosurgical Anesthesiology, vol. 10, No. 2, pp. 106-112, May 1998.

Hori et al., "Arterial pressure above the upper cerebral autoregulation limit during cardiopulmonary bypass is associated with post-operative delirium," British Journal of Anaesthesia Sep. 2014, pp. 1009-1017.

Kamar et al., "Detecting Cerebral Autoregulation Thresholds Using a Noninvasive Cerebral Flow Monitor," Ornim medical, May 2013, Portugal Poster, 1 pp.

Lucas et al., "Influence of Changes in Blood Pressure on cerebral Perfusion and Oxygenation," Hypertension, Oct. 2009, pp. 698-705.

Minassian et al., "Changes in intracranial pressure and cerebral autoregulation in patients with severe traumatic brain injury," vol. 30, Jul. 2002, pp. 1616-1622.

Pesek, MD, et al., "The upper limit of cerebral blood flow autoregulation is decreased with elevations in intracranial pressure," Neurosurgery, vol. 75, No. 2, Aug. 2014, pp. 163-170.

Sadoshima et al., "Upper Limit of Cerebral Autoregulation During Development of Hypertension in Spontaneously Hypertensive Rats—Effect of Sympathetic Denervation," vol. 16, No. 3, May-Jun. 1985, pp. 477-481.

Sadoshima et al., "Inhibition of Angiotensin—Converting Enzyme Modulates the Autoregulation of Regional Cerebral Blood Flow in Hypertensive Rats," vol. 23, No. 6, Part 1, Jun. 1994, pp. 781-785.

Strandgaard et al., "Upper Limit of Cerebral Blood Flow Autoregulation in Experimental Renovascular Hypertension in the Baboon," vol. 37, Aug. 1975, pp. 164-167.

Ragauskas et al., "Analysis of cerebrovascular autoregulation reactivity index electronic monitoring methods," vol. 114, No. 8, Jun. 2011, 6 pp.

Chiu et al., "Assessment of cerebral autoregulation using time-domain cross-correlation analysis," Computers Bio Med, Nov. 2001, pp. 471-480.

Larson et al., "Cerebrovascular autoregulation after rewarming from hypothermia in a neonatal swine model of asphyxic brain injury," J Appl Physiol. 115; pp. 1433-1442, Sep. 2013.

Petkus et al., "Novel Method and Device for Fully Non-Invasive Cerebrovascular Autoregulation Monitoring," Elektronika Ir Elektrotechnika, vol. 20, No. 8, pp. 24-29, Oct. 2014.

Olufsen et al., "Blood pressure and blood flow variation during postural change from sitting to standing: model development and validation," J Appl Physiol Oct. 2005, pp. 1523-1537.

Rangel-Castilla, MD, et al., "Cerebral pressure autoregulation in traumatic brain injury," Neurosurg Focus, vol. 25, Oct. 2008, 8 pp.

Addison, "A Review of Wavelet Transform Time-Frequency Methods for NIRS-Based Analysis of Cerebral Autoregulation," IEEE Reviews in Biomedical Engineering, vol. 8, 2015, pp. 78-85.

Moerman, M.D., Ph.D., et al., "Assessment of Cerebral Autoregulation Patterns with Near-infrared Spectroscopy during Pharmacological-induced Pressure Changes," Anesthesiology, vol. 123, No. 2, Aug. 2015, pp. 327-335.

U.S. Appl. No. 15/911,449, naming Paul S. Addison et al. as inventors, filed Mar. 5, 2018.

U.S. Appl. No. 15/962,438, naming Paul S. Addison et al. as inventors, filed Apr. 25, 2018.

U.S. Appl. No. 15/980,235, naming Paul S. Addison et al. as inventors, filed May 15, 2018.

U.S. Appl. No. 15/962,503, naming Paul S. Addison et al. as inventors, filed Apr. 25, 2018.

U.S. Appl. No. 15/962,486, naming Dean Montgomery et al. as inventors, filed Apr. 25, 2018.

Chuan et al., "Is cerebrovascular autoregulation associated with outcomes after major noncardiac surgery? A prospective observational pilot study," Acta Anaesthesiol Scand., Aug. 5, 2018, 10 pp.

\* cited by examiner

DETERMINING CHANGES TO AUTOREGULATION

TECHNICAL FIELD

This disclosure relates to physiological parameter monitoring.

BACKGROUND

Cerebral autoregulation (CA) is the response mechanism by which an organism regulates cerebral blood flow over a wide range of systemic blood pressure changes through complex myogenic, neurogenic, and metabolic mechanisms. Autoregulation dysfunction may result from a number of causes including, stroke, traumatic brain injury, brain lesions, brain asphyxia, or infections of the central nervous system. Intact cerebral autoregulation function occurs over a range of blood pressures defined between a lower limit of autoregulation (LLA) and an upper limit of autoregulation (ULA).

SUMMARY

This disclosure describes devices, systems, and techniques including processing circuitry configured to determine an estimate of a limit of autoregulation by at least determining a metric of correlation coefficient values for each bin of a plurality of bins. The processing circuitry may define a bin (e.g., a data bin or data bucket) as including those correlation coefficient values associated with values of a physiological parameter within the bin. The processing circuitry may adjust parameters of the bins such that the particular correlation coefficient values falling within respective bins varies. Example bin parameters may include bin width and separation distance between bins. For example, each bin of the plurality of bins may have a width in terms of a physiological parameter, such as the mean arterial pressure or the oxygen saturation of the patient. The width of each bin may span from a minimum value of the physiological parameter for the bin to a maximum value of the physiological parameter for the bin. The processing circuitry may determine a width of less than five millimeters of mercury (mmHg) for each bin, in some examples, such as when the first physiological parameter is mean arterial pressure. The center of a bin may be offset from an adjacent bin by a separation distance defined in terms of the first physiological parameter.

The metric associated with a bin may be a value that represents the correlation coefficient values in the bin (e.g., a mean, a weighted average, and/or a median of the correlation coefficient values). The processing circuitry may determine the metric associated with each bin by, for example, determining a mean, weighted average, or a median of the correlation coefficients values associated with values of the physiological parameter between the minimum value and the maximum value. For example, the processing circuitry may determine the metric for a bin centered on 50 mmHg with a width of two mmHg by selecting the correlation coefficients values associated with values of the physiological parameter between 49 and 51 mmHg.

The processing circuitry may also be configured to determine, e.g., for the same correlation coefficient values determined based on a set of data collected over a time period, the metric of the correlation coefficient values for each bin of a second plurality of bins where each bin of the second plurality of bins has a bin parameter different than the bin parameter of the first plurality of bins. The processing circuitry can determine a composite estimate of the limit of autoregulation based on the metric of the correlation coefficient values for each plurality of bins.

Clause 1: In some examples, a device comprises a display and processing circuitry configured to receive a first signal indicative of a first physiological parameter of a patient and a second signal indicative of a second physiological parameter of the patient. The processing circuitry is also configured to determine a set of correlation coefficient values for a set of values of the first physiological parameter and for a set of values of the second physiological parameter. The processing circuitry is further configured to determine a metric of the correlation coefficient values for each bin of a first plurality of bins and for each bin of a second plurality of bins. Each bin of the first plurality of bins has a first bin parameter defined in terms of the first physiological parameter, each bin of the second plurality of bins has a second bin parameter defined in terms of the first physiological parameter, the second bin parameter being different than the first bin parameter. The processing circuitry is configured to determine a composite estimate of a limit of autoregulation of the patient based on the metric of the correlation coefficient values for the first plurality of bins and the metric of the correlation coefficient values for the second plurality of bins. The processing circuitry is also configured to determine an autoregulation status of the patient based on the composite estimate of the limit of autoregulation and output, for display via the display, an indication of the autoregulation status.

Clause 2: In some examples of clause 1, the processing circuitry is configured to determine the composite estimate of the limit of autoregulation at least in part by determining a first estimate of the limit of autoregulation based on the metric of the correlation coefficient values for the first plurality of bins, determining a second estimate of the limit of autoregulation based on the metric of the correlation coefficient values for the second plurality of bins, and determining the composite estimate of the limit of autoregulation based on the first estimate of the limit of autoregulation and the second estimate of the limit of autoregulation.

Clause 3: In some examples of clause 2, the processing circuitry is configured to determine the composite estimate at least in part by determining an average of the first estimate of the limit of autoregulation and the second estimate of the limit of autoregulation.

Clause 4: In some examples of clause 2 or clause 3, the processing circuitry is configured to determine the composite estimate of the limit of autoregulation at least in part by determining a confidence measure for the first estimate of the limit of autoregulation and the second estimate of the limit of autoregulation. The processing circuitry is configured to determine the autoregulation status at least in part by determining a weighting factor for the composite estimate of the limit of autoregulation based on the confidence measure.

Clause 5: In some examples of clause 4, the processing circuitry is configured to determine the weighting factor such that the composite estimate is weighted higher in a first instance when the first estimate is equal to the second estimate than in a second instance when the first estimate is not equal to the second estimate.

Clause 6: In some examples of any of clauses 2-5, the limit of autoregulation is a lower limit of autoregulation, and wherein the processing circuitry is configured to determine the composite estimate of the lower limit of autoregulation at least in part by determining a lowest value of the first physiological parameter at which the metric of the correlation coefficient values is less than a threshold level.

Clause 7: In some examples of any of clauses 1-6, the first bin parameter comprises a first width, and the second bin parameter comprises a second width. Each width of the first width and the second width is defined by a difference of a respective minimum value of the first physiological parameter and a respective maximum value of the first physiological parameter. The processing circuitry is configured to determine the metric of the correlation coefficient values at least in part by determining the metric of the correlation coefficient values associated with values of the first physiological parameter in a range of greater than the respective minimum value and less than the respective maximum value.

Clause 8: In some examples of any of clauses 1-7, the metric of the correlation coefficient values comprises a median of the correlation coefficient values within the respective bin of the set of bins.

Clause 9: In some examples of any of clauses 1-8, the metric of the correlation coefficient values comprises a mean of the correlation coefficient values within the respective bin of the set of bins.

Clause 10: In some examples of any of clauses 1-9, the first bin parameter comprises a first width, the second bin parameter comprises a second width, and at least one of the first width or the second width is less than or equal to four mmHg.

Clause 11: In some examples of clause 10, wherein at least one of the first width or the second width is in a range of greater than or equal to one mmHg and less than or equal to three mmHg.

Clause 12: In some examples of any of clauses 1-11, the first bin parameter comprises a first distance by which a center of each bin of the first plurality of bins is offset from a center of an adjacent bin of the first plurality of bins. The second bin parameter comprises a second distance by which a center of each bin of the second plurality of bins is offset from a center of an adjacent bin of the second plurality of bins, the second distance being different than the first distance.

Clause 13: In some examples of clause 12, at least one of the first distance or the second distance is less than or equal to four millimeters of mercury mmHg.

Clause 14: In some examples of clause 12 or clause 13, at least one of the first distance or the second distance is in a range of greater than or equal to one millimeters of mercury (mmHg) and less than or equal to three mmHg.

Clause 15: In some examples of any of clauses 1-14, the processing circuitry is configured to determine the metric of the correlation coefficient values for each respective bin of the first plurality of bins at least in part by determining a first mean and a standard deviation of the correlation coefficient values for the respective bin, determining an outlier correlation coefficient that is greater than three times the standard deviation from the first mean, and determining a second mean of the correlation coefficient values, excluding the outlier correlation coefficient, for the respective bin.

Clause 16: In some examples, a method comprises receiving, by processing circuitry and from sensing circuitry, a first signal indicative of a first physiological parameter of a patient and a second signal indicative of a second physiological parameter of the patient. The method also comprises determining, by the processing circuitry, a set of correlation coefficient values for a set of values of the first physiological parameter and for a set of values of the second physiological parameter. The method further comprises determining, by the processing circuitry, a metric of the correlation coefficient values for each bin of a first plurality of bins and for each bin of a second plurality of bins, wherein each bin of the first plurality of bins has a first bin parameter defined in terms of the first physiological parameter, and each bin of the second plurality of bins has a second bin parameter defined in terms of the first physiological parameter, the second bin parameter being different than the first bin parameter. The method comprises determining, by the processing circuitry, a composite estimate of a limit of autoregulation of the patient based on the metric of the correlation coefficient values for the first plurality of bins and the metric of the correlation coefficient values for the second plurality of bins. The method also comprises determining, by the processing circuitry, an autoregulation status of the patient based on the composite estimate of the limit of autoregulation and outputting, by the processing circuitry for display via the display, an indication of the autoregulation status.

Clause 17: In some examples, a device comprises a display and processing circuitry configured to receive a first signal indicative of a first physiological parameter of a patient and a second signal indicative of a second physiological parameter of the patient. The processing circuitry is also configured to determine a set of correlation coefficient values for a set of values of the first physiological parameter and for a set of values of the second physiological parameter. The processing circuitry is further configured to determine a metric of the correlation coefficient values for each bin of a first plurality of bins at least in part by determining a first weighting factor for each correlation coefficient, where each bin of the first plurality of bins has a first bin parameter defined in terms of the first physiological parameter. The processing circuitry is also configured to determine a metric of the correlation coefficient values for each bin of a second plurality of bins at least in part by determining a second weighting factor for each correlation coefficient, where each bin of the second plurality of bins has a second bin parameter defined in terms of the first physiological parameter, the second bin parameter being different than the first bin parameter. The processing circuitry is configured to determine a composite estimate of a limit of autoregulation of the patient based on the metric of the correlation coefficient values for the first plurality of bins and the metric of the correlation coefficient values for the second plurality of bins. The processing circuitry is also configured to determine an autoregulation status of the patient based on the composite estimate of the limit of autoregulation and output, for display via the display, an indication of the autoregulation status.

Clause 18: In some examples of clause 17, the processing circuitry is configured to determine the first weighting factor based on an age of each correlation coefficient within the respective bin such that more recent correlation coefficient values are weighted higher than less recent correlation coefficient values. The processing circuitry is configured to determine the second weighting factor based on the age of each correlation coefficient within the respective bin such that more recent correlation coefficient values are weighted higher than less recent correlation coefficient values.

Clause 19: In some examples of clause 17 or clause 18, the processing circuitry is configured to determine the first weighting factor based on a distance between a center of a bin of the first plurality of bins and a value of the first physiological parameter associated with the respective correlation coefficient such that correlation coefficient values closer to the center of the bin are weighted higher than correlation coefficient values farther from the center of the bin. The processing circuitry is configured to determine the second weighting factor based on a distance between a center of a bin of the second plurality of bins and the value of the first physiological parameter associated with the respective correlation coefficient such that correlation coefficient values closer to the center of the bin are weighted higher than correlation coefficient values farther from the center of the bin.

Clause 20: In some examples of any of clauses 17-19, the processing circuitry is configured to determine the first weighting factor based on a signal quality metric. The processing circuitry is configured to determine the second weighting factor based on the signal quality metric.

Clause 21: In some examples, a device comprises sensing circuitry configured to receive a first signal indicative of a first physiological parameter of a patient and a second signal indicative of a second physiological parameter of the patient. The device also comprises processing circuitry configured to determine a set of correlation coefficient values for a set of values of the first physiological parameter and for a set of values of the second physiological parameter. The processing circuitry is further configured to determine a metric of the correlation coefficient values for each bin of a first plurality of bins and for each bin of a second plurality of bins. Each bin of the first plurality of bins has a first bin parameter defined in terms of the first physiological parameter, each bin of the second plurality of bins has a second bin parameter defined in terms of the first physiological parameter, the second bin parameter being different than the first bin parameter. The processing circuitry is configured to determine a composite estimate of a limit of autoregulation of the patient based on the metric of the correlation coefficient values for the first plurality of bins and the metric of the correlation coefficient values for the second plurality of bins. The processing circuitry is also configured to determine an autoregulation status of the patient based on the composite estimate of the limit of autoregulation and output, for display via a display, an indication of the autoregulation status.

The details of one or more examples are set forth in the accompanying drawings and the description below. Other features, objects, and advantages will be apparent from the description and drawings, and from the claims.

DETAILED DESCRIPTION

Figure 1:
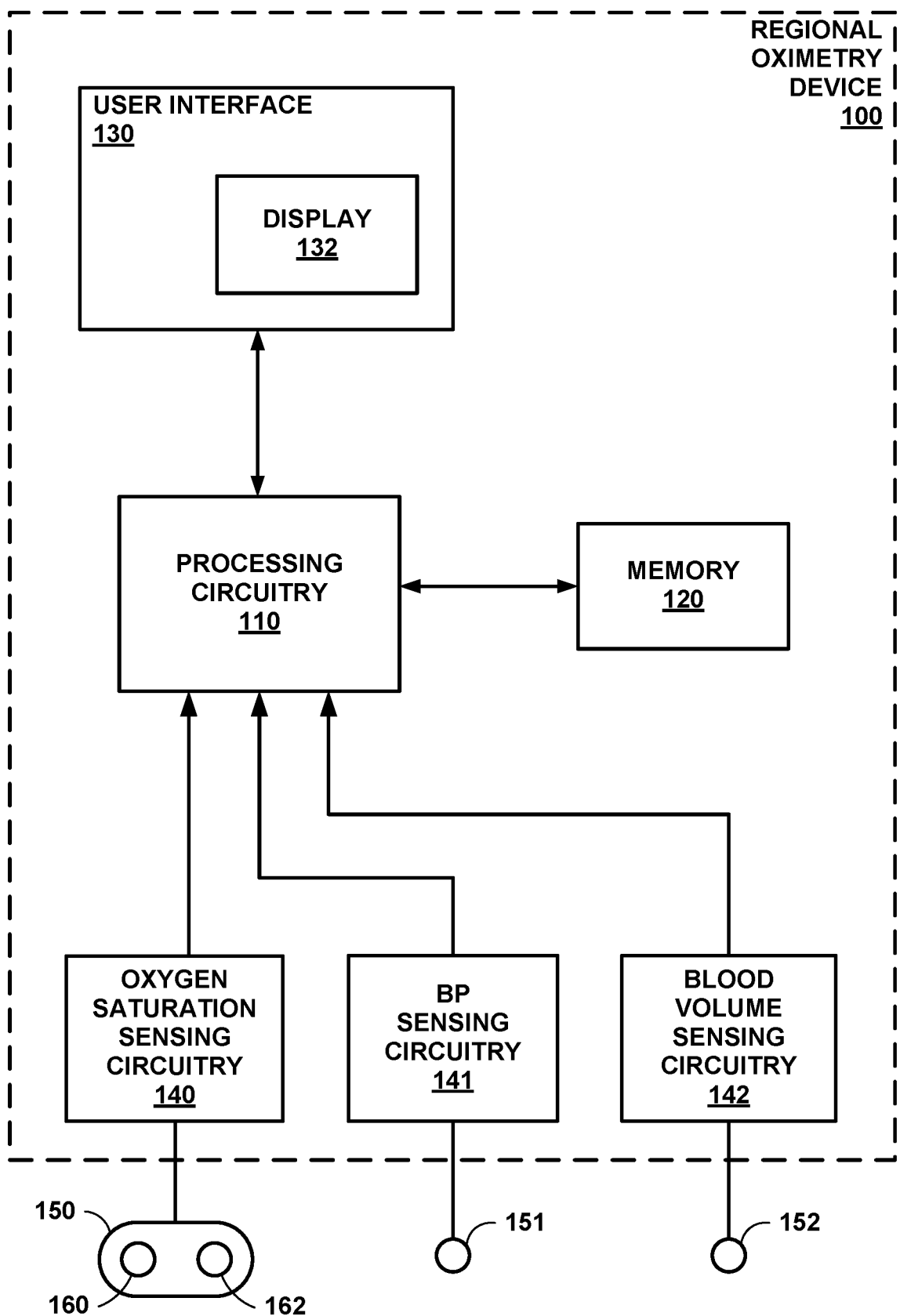
FIG. 1 is a conceptual block diagram illustrating an example regional oximetry device.

This disclosure describes devices, systems, and techniques for determining changes in cerebral autoregulation of a patient. A system may include a regional oximetry device that includes processing circuitry configured to determine the cerebral autoregulation status of the patient based on a limit of autoregulation, also referred to as a limit of cerebral autoregulation, such as the lower limit of autoregulation (LLA) and/or the upper limit of autoregulation (ULA). To determine the LLA and/or the ULA, the processing circuitry is configured to determine correlation coefficient values based on two physiological parameters. The two physiological parameters may include blood pressure, mean arterial pressure, oxygen saturation, blood volume, and/or any other physiological parameters.

The processing circuitry may define bin parameters of one or more bins (e.g., data bins or data buckets) that will include those correlation coefficient values associated with values of a physiological parameter within the width of a bin. The bin parameters may be defined in terms of pre-defined values of the physiological parameters. The processing circuitry may create each bin as a logical container, defined by bin parameters, that holds groups of zero or more correlation coefficient values. Each bin can contain a group of correlation coefficient values that are associated with similar values of the first physiological parameter. The processing circuitry may define bin parameters (e.g., width and/or separation distance) for the first plurality of bins such that every correlation coefficient falls within one or more bins. For example, the processing circuitry may determine a first bin centered at a value of one hundred with a width of ten units (e.g., mmHg). The processing circuitry can determine correlation coefficient values associated with (that fall within) the bin by selecting all of the correlation coefficient values associated with values of the first physiological parameter between 95 and 105. The processing circuitry may be configured to determine a metric of the correlation coefficient values for each bin of a first plurality of bins and for each bin of a second plurality of bins.

The processing circuitry may define one or more bin parameters including, for example, bin width, distance between bin centers, maximum age of correlation coefficient values, maximum number of correlation coefficient values per bin, or other bin parameters defining a characteristic of data bins. For example, each bin of the first plurality of bins may have a first width defined in terms of one of the two physiological parameters, and each bin of the second plurality of bins may have a second width. The processing circuitry may determine respective estimates of the limit of autoregulation based on the metric for the first plurality of bins and based on the metric for the second plurality of bins. The processing circuitry may then use the first and second estimates to determine a composite estimate of the limit of autoregulation and determine an autoregulation status of a patient based on the composite estimate. The processing circuitry may be further configured to output, for display, an indication of the composite estimate of the limit of autoregulation and/or an indication of the autoregulation status.

The width of the bins or other bin parameters may affect the resulting estimate of the limit of autoregulation. For example, the metrics of bins with relatively large widths may less accurately show the value of the first physiological parameter at which the correlation coefficient value decreases below a threshold value. In accordance with the techniques of this disclosure, the processing circuitry may determine multiple, different estimates based on pluralities of bins with different widths. The processing circuitry can use the multiple, different estimates to determine a composite estimate that may be more accurate than a single estimate. In some examples, if all of the estimates of the limit of autoregulation are relatively close, the processing circuitry may determine the composite estimate as the mean or the median of the estimates and assign a relatively high confidence measure to the composite estimate.

In contrast, if the estimates of the limit of autoregulation are relatively far apart, the processing circuitry may determine a composite estimate with a relatively low confidence measure indicating that the composite estimate may be less accurate. The processing circuitry may use the confidence measure to determine the weighting of each estimate on the determination of the composite measure.

In some examples, the composite estimate may be a weighted average of the current estimates and previous composite estimates. The processing circuitry may be configured to weight the current estimates based on the confidence measure, such that, if all of the current estimates of the limit of autoregulation are relatively close, the processing circuitry may weight the current estimates more heavily than if the estimates of the limit of autoregulation relatively far apart. The processing circuitry may "weight" an estimate by determining a weighting factor for the estimate and multiplying the estimate and the weighting factor to determine a weighted value.

A patient state, as indicated by sensed physiological signals, may change relatively rapidly over time. In response to a changing patient state, some estimates of a limit of autoregulation may change quickly, while other estimates may change slowly. Even if the patient state does not change, an inaccurate estimate of the limit of autoregulation can change rapidly. Processing circuitry that uses multiple, different estimates can reduce the weighting of outlier estimates and other inaccurate estimates. The processing circuitry may determine a composite estimate of the limit of autoregulation that is more accurate, as compared to processing circuitry determines only one estimate of the limit of autoregulation based on bins with a width of five millimeters of mercury (mmHg).

The devices, systems, and techniques of this disclosure may increase the accuracy of the presentation of an estimate of a limit of autoregulation of a patient and the presentation of an indication of the autoregulation status of the patient. The presentation of more accurate and more stable information may result in increased confidence by a clinician viewing the presented information, which may lead to more informed decision making by the clinician. A clinician may lose confidence in the information presented by the processing circuitry if the information is unstable and/or inaccurate. By using a composite estimate to determine an autoregulation status, the processing circuitry may present more accurate autoregulation indications, as compared to another device that uses a single estimate. By presenting a composite estimate of a limit of autoregulation, the processing circuitry may generate a simpler and easier-to-use display for a user, as compared to presenting multiple individual estimates.

The autoregulation status of a patient may be an indication that the cerebral autoregulation control mechanism of the patient is intact (e.g., functioning properly) or impaired (e.g., not functioning properly). A cerebral autoregulation control mechanism of the body may regulate cerebral blood flow (CBF) over a range of systemic blood pressures. This range of systemic blood pressures may lie within a lower limit of autoregulation (LLA) and an upper limit of autoregulation (ULA). Outside of the LLA and the ULA, blood pressure directly drives CBF, and cerebral autoregulation function may thus be considered impaired.

One method to determine the limits of autoregulation (e.g., the LLA and ULA) noninvasively using near-infrared spectroscopy (NIRS) technology may include the COx measure, which is a moving correlation index between mean arterial pressure (MAP) and regional oxygen saturation ($rSO_2$). The COx measure (e.g., the Pearson coefficient) is derived from the correlation between $rSO_2$ and MAP. COx relates to the regression line fit or linear correlation between $rSO_2$ and MAP over a time window having a particular length, such as three hundred seconds, in some examples. The COx method may be used to produce a representation of a patient's blood-pressure-dependent autoregulation status.

When the cerebral autoregulation is intact for a patient, there is typically no correlation between MAP and $rSO_2$. In contrast, MAP and $rSO_2$ typically directly correlate (e.g., the correlation index of COx is approximately 1) when the cerebral autoregulation is impaired. In practice, however, sensed data indicative of autoregulation may be noisy and/or there might be a slightly correlated relationship between variables (e.g., MAP and $rSO_2$) even when cerebral autoregulation is intact for the patient.

Some existing systems for monitoring autoregulation may determine a patient's autoregulation status based on various physiological parameter values (also referred to herein as physiological values). Such physiological values may be subject to various sources of error, such as noise caused by relative sensor and patient motion, operator error, poor quality measurements, drugs, or other anomalies. However, some existing systems for monitoring autoregulation may not reduce the various sources of error when utilizing the measured physiological values to determine the patient's autoregulation status. Furthermore, some existing systems may not determine and/or utilize a reliable metric to determine whether the autoregulation status calculated from the physiological values is reliable. Accordingly, the autoregulation status determined by such existing systems may be less accurate or less reliable.

In an intact region of cerebral autoregulation, there may be no correlation between these variables whereas in an impaired region of cerebral autoregulation, the correlation index should approximate unity. In practice, however, the data may be noisy and/or the intact region may exhibit a slightly positive relationship. This positive relationship may render traditional autoregulation limit calculations difficult to perform, resulting in the need for manual interpretation of the data using arbitrary thresholds. Further, the underlying mathematics of the technique may be asymmetric in terms of the results produced for impaired and intact regions and may be, in fact, not computable for the ideal case within the intact region.

A physician may monitor a patient's autoregulation through the use of various monitoring devices and systems that measure various physiological parameters. In certain aspects of the present disclosure, a patient's autoregulation may be monitored by correlating measurements of the patient's blood pressure (e.g., arterial blood pressure) with measurements of the patient's oxygen saturation (e.g., regional oxygen saturation). In particular, a cerebral oximetry index (COx) may be derived based at least in part on a linear correlation between the patient's blood pressure and oxygen saturation. In addition, in certain aspects of the present disclosure, the patient's autoregulation may be monitored by correlating measurements of the patient's blood pressure with measurements of the patient's blood volume (e.g., blood volume proxy). In particular, a hemoglobin volume index (HVx) may be derived based at least in part on a linear correlation between the patient's blood pressure and blood volume.

While features of the present disclosure are discussed with reference to COx, in other examples, various other linear correlations such as HVx may be determined to help evaluate a patient's autoregulation status. For example, a linear correlation between measurements of a patient's blood pressure and measurements of a patient's cerebral blood flow may derive a mean velocity index (Mx). As a further example, a linear correlation between measurements of a patient's blood pressure and measurements of a patient's intracranial pressure may derive a pressure reactivity index (PRx). In certain situations, these indexes may be utilized to determine or help evaluate a patient's autoregulation. The devices, systems, and techniques of this disclosure can also be applied to the determination of indices such as HVx, Mx, PRx, and/or any other indices, coefficients, and correlations. For example, processing circuitry may be configured to determine a composite estimate of a limit of autoregulation based on a metric for two or more pluralities of bins of HVx indices, Mx indices, or PRx indices.

Additional example details of the physiological parameters that can be used for determining a limit of autoregulation may be found in commonly assigned U.S. Patent Application Publication No. 2016/0367197 filed on Jun. 16, 2016, entitled "Systems and Methods for Reducing Signal Noise When Monitoring Autoregulation," and commonly assigned U.S. Patent Application Publication No. 2017/0105631 filed on Oct. 18, 2016, entitled "System and Method for Providing Blood Pressure Safe Zone Indication During Autoregulation Monitoring," which are incorporated herein by reference in their entirety.

FIG. 1 is a conceptual block diagram illustrating an example regional oximetry device 100. Regional oximetry device 100 includes processing circuitry 110, memory 120, user interface 130, display 132, sensing circuitry 140-142, and sensing device(s) 150-152. In some examples, regional oximetry device 100 may be configured to determine and display the cerebral autoregulation status of a patient, e.g., during a medical procedure or for more long-term monitoring, such as fetal monitoring. A clinician may receive information regarding the cerebral autoregulation status of a patient via display 132 and adjust treatment or therapy to the patient based on the cerebral autoregulation status information.

Processing circuitry 110, as well as other processors, processing circuitry, controllers, control circuitry, and the like, described herein, may include one or more processors. Processing circuitry 110 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Memory 120 may be configured to store measurements of physiological parameters, MAP values, $rSO_2$ values, COx values, and value(s) of an LLA and/or a ULA, for example. Memory 120 may also be configured to store data such as metrics, bin parameters such as widths and separation distances between centers of adjacent bins, weighting factors, and/or threshold levels for metrics. The metrics, widths, separation distances between centers of adjacent bins, weighting factors, and/or threshold levels may stay constant throughout the use of device 100 and across multiple patients, or these values may change over time.

In some examples, memory 120 may store program instructions, which may include one or more program modules, which are executable by processing circuitry 110. When executed by processing circuitry 110, such program instructions may cause processing circuitry 110 to provide the functionality ascribed to it herein. The program instructions may be embodied in software, firmware, and/or RAMware. Memory 120 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

User interface 130 and/or display 132 may be configured to present information to a user (e.g., a clinician). User interface 130 and/or display 132 may be configured to present a graphical user interface to a user, where each graphical user interface may include indications of values of one or more physiological parameters of a patient. For example, processing circuitry 110 may be configured to present blood pressure values, physiological parameter values, and indications of autoregulation status (e.g., cerebral autoregulation status) of a patient via display 132. In some examples, if processing circuitry 110 determines that the autoregulation status of the patient is impaired, then processing circuitry 110 may present a notification (e.g., an alert) indicating the impaired cerebral autoregulation status via display 132. As another example, processing circuitry 110 may present, via display 132, estimates of $rSO_2$ for a patient, an estimate of the blood oxygen saturation ($SpO_2$) determined by processing circuitry 110, pulse rate information, respiration rate information, blood pressure, any other patient parameters, or any combination thereof.

User interface 130 and/or display 132 may include a monitor, cathode ray tube display, a flat panel display such as a liquid crystal (LCD) display, a plasma display, a light emitting diode (LED) display, and/or any other suitable display. User interface 130 and/or display 132 may be part of a personal digital assistant, mobile phone, tablet computer, laptop computer, any other suitable computing device, or any combination thereof, with a built-in display or a separate display. User interface 130 may also include means for projecting audio to a user, such as speaker(s). Processing circuitry 110 may be configured to present, via user interface 130, a visual, audible, tactile, or somatosensory notification (e.g., an alarm signal) indicative of the patient's autoregulation status and/or a notification indicative of the patient's limit(s) of autoregulation.

User interface 130 may include or be part of any suitable device for conveying such information, including a computer workstation, a server, a desktop, a notebook, a laptop, a handheld computer, a mobile device, or the like. In some examples, processing circuitry 110 and user interface 130 may be part of the same device or supported within one housing (e.g., a computer or monitor). In other examples, processing circuitry 110 and user interface 130 may be separate devices configured to communicate through a wired connection or a wireless connection (e.g., communication interface 290 shown in FIG. 2).

Sensing circuitry 140-142 may be configured to receive physiological signals sensed by respective sensing device(s) 150-152 and communicate the physiological signals to processing circuitry 110. Sensing device(s) 150-152 may include any sensing hardware configured to sense a physiological parameter of a patient, such as, but not limited to, one or more electrodes, optical receivers, blood pressure cuffs, or the like. Sensing circuitry 140-142 may convert the physiological signals to usable signals for processing circuitry 110, such that processing circuitry 110 is configured to receive signals generated by sensing circuitry 140-142. Sensing circuitry 140-142 may receive signals indicating physiological parameters from a patient, such as, but not limited to, blood pressure, regional oxygen saturation, blood volume, heart rate, and respiration. Sensing circuitry 140-142 may include, but are not limited to, blood pressure sensing circuitry, oxygen saturation sensing circuitry, blood volume sensing circuitry, heart rate sensing circuitry, temperature sensing circuitry, electrocardiography (ECG) sensing circuitry, electroencephalogram (EEG) sensing circuitry, or any combination thereof. In some examples, sensing circuitry 140-142 and/or processing circuitry 110 may include signal processing circuitry such as an analog-to-digital converter.

In some examples, oxygen saturation sensing device 150 is a regional oxygen saturation sensor configured to generate an oxygen saturation signal indicative of blood oxygen saturation within the venous, arterial, and/or capillary systems within a region of the patient. For example, oxygen saturation sensing device 150 may be configured to be placed on the patient's forehead and may be used to determine the oxygen saturation of the patient's blood within the venous, arterial, and/or capillary systems of a region underlying the patient's forehead (e.g., in the cerebral cortex).

In such cases, oxygen saturation sensing device 150 may include emitter 160 and detector 162. Emitter 160 may include at least two light emitting diodes (LEDs), each configured to emit at different wavelengths of light, e.g., red or near infrared light. In some examples, light drive circuitry (e.g., within sensing device 150, sensing circuitry 140, and/or processing circuitry 110) may provide a light drive signal to drive emitter 160 and to cause emitter 160 to emit light. In some examples, the LEDs of emitter 160 emit light in the wavelength range of about 600 nanometers (nm) to about 1000 nm. In a particular example, one LED of emitter 160 is configured to emit light at a wavelength of about 730 nm and the other LED of emitter 160 is configured to emit light at a wavelength of about 810 nm. Other wavelengths of light may also be used in other examples.

Detector 162 may include a first detection element positioned relatively "close" (e.g., proximal) to emitter 160 and a second detection element positioned relatively "far" (e.g., distal) from emitter 160. Light intensity of multiple wavelengths may be received at both the "close" and the "far" detector 162. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation signal for the target tissues over time. Oxygen saturation sensing device 150 may provide the regional oxygen saturation signal to processing circuitry 110 or to any other suitable processing device to enable evaluation of the patient's autoregulation status.

In operation, blood pressure sensing device 151 and oxygen saturation sensing device 150 may each be placed on the same or different parts of the patient's body. For example, blood pressure sensing device 151 and oxygen saturation sensing device 150 may be physically separate from each other and may be separately placed on the patient. As another example, blood pressure sensing device 151 and oxygen saturation sensing device 150 may in some cases be part of the same sensor or supported by a single sensor housing. For example, blood pressure sensing device 151 and oxygen saturation sensing device 150 may be part of an integrated oximetry system configured to non-invasively measure blood pressure (e.g., based on time delays in a PPG signal) and regional oxygen saturation. One or both of blood pressure sensing device 151 or oxygen saturation sensing device 150 may be further configured to measure other physiological parameters, such as hemoglobin, respiratory rate, respiratory effort, heart rate, saturation pattern detection, response to stimulus such as bispectral index (BIS) or electromyography (EMG) response to electrical stimulus, or the like. While an example regional oximetry device 100 is shown in FIG. 1, the components illustrated in FIG. 1 are not intended to be limiting. Additional or alternative components and/or implementations may be used in other examples.

Blood pressure sensing device 151 may be any sensor or device configured to obtain the patient's blood pressure (e.g., arterial blood pressure). For example, blood pressure sensing device 151 may include a blood pressure cuff for non-invasively monitoring blood pressure or an arterial line for invasively monitoring blood pressure. In certain examples, blood pressure sensing device 151 may include one or more pulse oximetry sensors. In some such cases, the patient's blood pressure may be derived by processing time delays between two or more characteristic points within a single plethysmography (PPG) signal obtained from a single pulse oximetry sensor.

Additional example details of deriving blood pressure based on a comparison of time delays between certain components of a single PPG signal obtained from a single pulse oximetry sensor are described in commonly assigned U.S. Patent Application Publication No. 2009/0326386 filed Sep. 30, 2008, and entitled "Systems and Methods for Non-Invasive Blood Pressure Monitoring," the entire content of which is incorporated herein by reference. In other cases, the patient's blood pressure may be continuously, non-invasively monitored via multiple pulse oximetry sensors placed at multiple locations on the patient's body. As described in commonly assigned U.S. Pat. No. 6,599,251, entitled "Continuous Non-invasive Blood Pressure Monitoring Method and Apparatus," the entire content of which is incorporated herein by reference, multiple PPG signals may be obtained from the multiple pulse oximetry sensors, and the PPG signals may be compared against one another to estimate the patient's blood pressure. Regardless of its form, blood pressure sensing device 151 may be configured to generate a blood pressure signal indicative of the patient's blood pressure (e.g., arterial blood pressure) over time. Blood pressure sensing device 151 may provide the blood pressure signal to sensing circuitry 141, processing circuitry 110, or to any other suitable processing device to enable evaluation of the patient's autoregulation status.

Processing circuitry 110 may be configured to receive one or more signals generated by sensing devices 150-152 and sensing circuitry 140-142. The physiological signals may include a signal indicating blood pressure, a signal indicating oxygen saturation, and/or a signal indicating blood volume of a patient (e.g., an isosbestic signal). Processing circuitry 110 may be configured to determine a set of values of a first physiological parameter and a set of values of a second physiological parameter based on two or more signals received by sensing devices 150-152 and sensing circuitry 140-142 and delivered to processing circuitry 110. Sensing devices 150-152 and sensing circuitry 140-142 can deliver the physiological signals directly to processing circuitry 110 or sensing circuitry 140-142 can modify the physiological signals (e.g., through pre-processing) before delivering signals to processing circuitry 110. The first and second physiological parameters may include mean arterial pressure, oxygen saturation, and/or blood volume. Processing circuitry 110 may associate each value in a set of values with a point in time. For example, processing circuitry 110 may determine a value of mean arterial pressure at a particular time based on the characteristics of a blood pressure signal over a time interval.

Processing circuitry 110 may then be configured to determine a set of correlation coefficient values for the set of values of the first physiological parameter and for the set of values of the second physiological parameter. Processing circuitry 110 may determine each correlation coefficient for a sample of the values of the first physiological parameter and for a sample of the values of the second physiological parameter. For example, processing circuitry 110 may determine each correlation coefficient based on a Pearson coefficient that measures the strength and direction of a linear relationship between the values of the first physiological parameter and for a sample of the values of the second physiological parameter.

Processing circuitry 110 may associate each correlation coefficient with a particular value of the first physiological parameter. As an example, processing circuitry 110 may associate each COx value or each HVx value with a particular value of MAP or another physiological parameter, as shown in FIGS. 4, 5, 6A-6C, and 7A-7G. FIG. 5 shows a set of correlation coefficient values plotted in terms of the associated value of the first physiological parameter. The values of the correlation coefficient values may range from negative one to positive one.

Processing circuitry 110 is configured to determine a metric of the correlation coefficient values for each bin of a plurality of bins (see discussion of FIGS. 4 and 5 below relating to the formation of bins). Processing circuitry 110 can also determine the width, minimum value, and maximum value of each bin in terms of the first physiological parameter. Processing circuitry 110 can also determine the separation distance between centers of adjacent bins in terms of the first physiological parameter. Processing circuitry 110 may be configured to determine the metric of the correlation coefficient values for each bin based on the correlation coefficient values that fall within the width of the bin. The metric may be a statistical measure of the values of the correlation coefficient values, such as the mean, median, or a weighted average.

For example, processing circuitry 110 may determine the following six COx values, where the first number in parenthesis is the COx value and the second number is the associated MAP value, in terms of mmHg: $COx_1=(1.0, 60)$, $COx_2=(0.8, 65)$, $COx_3=(0.9, 67)$, $COx_4=(0.4, 68)$, $COx_5=(0.7, 70)$, and $COx_6=(0, 72)$. Processing circuitry 110 may determine a first bin with width of two mmHg, centered at 66 mmHg, such that the bin has minimum value of 65 mmHg and a maximum value of 67 mmHg. Processing circuitry 110 then determines that the second and third COx values fall within the first bin and determines a metric (e.g., mean) of 0.85. Processing circuitry 110 can determine a second bin with a width of two mmHg centered at 68 mmHg. Processing circuitry 110 determines a metric of 0.65 for the second bin based on the third and fourth COx values.

Processing circuitry 110 can determine a third bin with a width of two mmHg centered at 70 mmHg. Processing circuitry 110 determines a metric of 0.7 for the third bin based on the fifth COx value. Processing circuitry 110 may use Equation (1) to determine the mean for the bins, where N equals two for the first and second bins and N equals one for the third bin.

$$\text{Mean} = \frac{1}{N}\sum_{i=1}^{N} COx_i \qquad (1)$$

Processing circuitry 110 may determine two or more respective pluralities of bins, where each of the respective pluralities of bins includes bins having a different bin parameter, such as width or separation distance between centers of adjacent bins. For example, processing circuitry 110 may determine a width of two mmHg for each bin in a first plurality of bins and a width of five mmHg for each bin in a second plurality of bins. In some examples, processing circuitry 110 determines that at least one of the first width or the second width is less than or equal to four mmHg. Processing circuitry 110 can also determine that at least one of the first width or the second width is in a range of greater than or equal to one mmHg and less than or equal to three mmHg.

In some examples, processing circuitry 110 alternatively or additionally determines a different separation distance between centers of adjacent bins in each respective plurality of bins. The separation distance is defined as the distance between the center of a first bin and the center of a second bin, where the first and second bins are adjacent (e.g., there are no other bins positioned between the first and second bins). In some examples, processing circuitry 110 determines that at least one of the first separation distance or the second separation distance is less than or equal to four mmHg. Processing circuitry 110 can also determine that at least one of the first separation distance or the second separation distance is in a range of greater than or equal to one mmHg and less than or equal to three mmHg.

Processing circuitry 110 may determine a separation distance of one mmHg for the first plurality of bins and a separation distance of two mmHg for the second plurality of bins. In some examples, processing circuitry 110 may determine only a single plurality of bins, where the width of each bin in the single plurality is less than five mmHg. Processing circuitry 110 may also determine a separation distance of less than five mmHg for the bins of the single plurality. Even using a single plurality of bins with widths of less than five mmHg, processing circuitry 110 may determine a more accurate estimate of a limit of autoregulation, as compared to another device using a single type of bin with widths and a separation distance between centers of adjacent bins of five mmHg.

A smaller separation distance between centers of adjacent bins may result in more bins over a range of values of the first physiological parameter. If the range of values of MAP is forty mmHg, a separation distance of five mmHg results in approximately eight bins, whereas a separation distance of one mmHg results in approximately forty bins. Thus, a smaller separation distance may be more processing intensive for processing circuitry 110 but the smaller separation distance may also produce more accurate results.

Processing circuitry 110 may determine an estimate of a limit of autoregulation based on the metric of the correlation coefficient values for each plurality of bins. The metric of the correlation coefficient values may be near positive one for bins centered at very low values and very high values of the first physiological parameter (see, e.g., FIG. 4). Therefore, in order to determine an estimate of the lower limit of autoregulation, processing circuitry 110 may determine the lowest value of the first physiological parameter that is associated with a bin with a metric below a threshold level, such as 0.8, 0.7, 0.6, 0.5, 0.4, 0.3, 0.2, 0.1, or 0.0. In order to determine an estimate of the upper limit of autoregulation, processing circuitry 110 may determine the highest value of the first physiological parameter that is associated with a bin with a metric below a threshold level. FIG. 4 shows an example of metrics near positive one at very high MAP values and very low MAP values and metrics less than a threshold level between the limits of autoregulation.

In some examples, processing circuitry 110 is further configured to determine a composite estimate of the limit of autoregulation of the patient based on the metric of the correlation coefficient values for the first plurality of bins and the metric of the correlation coefficient values for the second plurality of bins. Processing circuitry 110 can determine the composite estimate as the mean of the estimates of the limit of autoregulation based on each plurality of bins. Processing circuitry 110 may be configured to exclude outlier estimates from the determination of the composite estimate. In some examples, processing circuitry 110 may be configured to determine the composite estimate as a weighted average of a previous composite estimate and each current estimate of the limit of autoregulation (e.g., a first estimate based on a first plurality of bins, a second estimate based on a second plurality of bins, etc.).

In some examples, processing circuitry 110 may be configured to determine a confidence measure based on the first estimate and the second estimate, where the confidence measure can indicate the relative distance or closeness of the two estimates. For example, if the two estimates are close in value, processing circuitry 110 may determine a relatively high confidence measure that indicates a higher likelihood that the two estimates are accurate. Processing circuitry 110 may determine the confidence measure based on previous estimates in order to determine rapid changes in the estimates of the limit of autoregulation. Rapid changes in the estimates may indicate inaccuracies. In some examples, processing circuitry 110 can also determine estimates of the limit of autoregulation based on other indices and other autoregulation metrics (e.g., COx, HVx, PRx, Mx, etc.) and then determine the confidence measure based on all of the estimates. Processing circuitry 110 may use the confidence measure to determine the composite estimate of the limit of autoregulation by determining a weighted average of the estimates, including other estimates and previous estimates. A higher confidence measure may result in processing circuitry 110 using a higher weighting factor for one or both of the estimates of the limit of autoregulation.

In some examples, within each bin, processing circuitry 110 may weight each correlation coefficient by applying a weighting factor. For example, processing circuitry 110 may determine the weighting factor for a correlation coefficient based on the age of the correlation coefficient, such that more recent correlation coefficient values are weighted higher or more heavily than less recent correlation coefficient values. Weighting by age may result in a composite estimate that adapts more quickly to changes in autoregulation. Processing circuitry 110 may weight the data within a bin by the age of each correlation coefficient. For example, processing circuitry 110 may apply a down weighting to older data to better detect recent changes.

In some examples, processing circuitry 110 may alternatively or additionally determine the weighting factor for a correlation coefficient based on the distance of the correlation coefficient from the center of the bin, such that correlation coefficient values that are closer to the center are weighted higher or more heavily than correlation coefficient values that are farther from the center. Processing circuitry 110 may weight the data within a bin by the distance from each correlation coefficient to the center of the bin. For example, processing circuitry 110 may use a triangular function or Gaussian distribution (see Equations (3) and (4) below). Weighting by distance may result in metrics that more accurately represent the value of the correlation coefficient values at the center of each bin.

In some examples, processing circuitry 110 may alternatively or additionally determine the weighting factor for a correlation coefficient based on a signal quality metric for the correlation coefficient. Weighting by signal quality metric may cause processing circuitry 110 to use higher-quality correlation coefficient values and exclude or dampen the effects of lower-quality correlation coefficient values. Processing circuitry 110 may also weight the data within a bin by the determined quality using a signal quality metric computed concurrently when computing the data point.

Each plurality of bins may have a different bin parameter, where a width of each bin and a separation distance between centers of adjacent bins are examples of bin parameters. Other examples of bin parameters include the maximum age of the correlation coefficient values in a bin and the maximum number of correlation coefficient values in a bin. For example, a first plurality of bins may have a maximum age of one hundred seconds, two hundred seconds, or three hundred seconds, or any other length of time. Thus, to determine a metric for a bin, processing circuitry 110 may also use only the correlation coefficient values in the bin that are more recent than the maximum age. Processing circuitry 110 can determine a different maximum age for a second plurality of bins.

Processing circuitry 110 can also determine different maximum (and/or minimum) number of correlation coefficient values for each plurality of bins. Processing circuitry 110 can apply the maximum or minimum number to use only recent correlation coefficient values for a bin unless the bin has very few recent correlation coefficient values. That is, processing circuitry may include the most recent correlation coefficient values up to a maximum number of values, and exclude the remaining older correlation coefficient values from the bin. If the bin has very few recent correlation coefficient values, processing circuitry 110 can include older values, in addition to the more recent values, if the more recent values are insufficient to meet the minimum number of correlation coefficient values. In some examples, processing circuitry 110 may use correlation coefficient values outside of the default width parameter to meet the minimum number of correlation coefficient values.

The bin parameters need not be constant across time or across values of the first physiological parameter. Processing circuitry 110 may be configured to dynamically change a bin parameter for a plurality of bins over time. For example, processing circuitry 110 may shorten the maximum age in response to a trigger event. Processing circuitry may be configured to determine bin parameters based on values of the first physiological parameter. For example, processing circuitry 110 can use a smaller width and/or smaller separation distance for bins between the limits of autoregulation (e.g., for intact autoregulation statuses) because there may be more correlation coefficient values available for bins centered between the limits of autoregulation.

In some examples, processing circuitry 110 is also configured to determine an autoregulation status of the patient based on the composite estimate of the limit of autoregulation. In the example of a composite estimate of the lower limit of autoregulation, processing circuitry 110 may determine whether the current mean arterial pressure of the patient is greater than the composite estimate of the lower limit of autoregulation. If the current mean arterial pressure is greater than the composite estimate of the lower limit of autoregulation, then processing circuitry 110 can determine that the patient has intact autoregulation, unless the current mean arterial pressure is greater than the upper limit of autoregulation. By determining a composite estimate based on two estimates of the limit of autoregulation using at least two pluralities of bins, processing circuitry 110 may more accurately determine autoregulation status, as compared to another device that does not implement the techniques of this disclosure.

Processing circuitry 110 outputs, such as for display via display 132 of user interface 130, an indication of the autoregulation status. Display 132 may present a graphical user interface such as graphical user interface 300 shown in FIG. 3. As described in further detail below, graphical user interface 300 includes an indicator of autoregulation status 350. The indication of autoregulation status may include text, colors, and/or audio presented to a user. Processing circuitry 110 may be further configured to present an indication of one or more limits of autoregulation (e.g., indicators 360 and 370).

Although other example techniques are possible, regional oximetry device 100 may be configured to determine the first estimate of the limit of autoregulation based on COx values derived from MAP values and $rSO_2$ values. Alternatively, processing circuitry 110 may determine the first estimate of the limit of autoregulation based on HVx values, BVS values, and/or $rSO_2$ values. Regional oximetry device 200 of FIG. 2 includes additional detail on how processing circuitry 110 can determine $rSO_2$ values based on a physiological signal received from sensing device 150.

Figure 2:
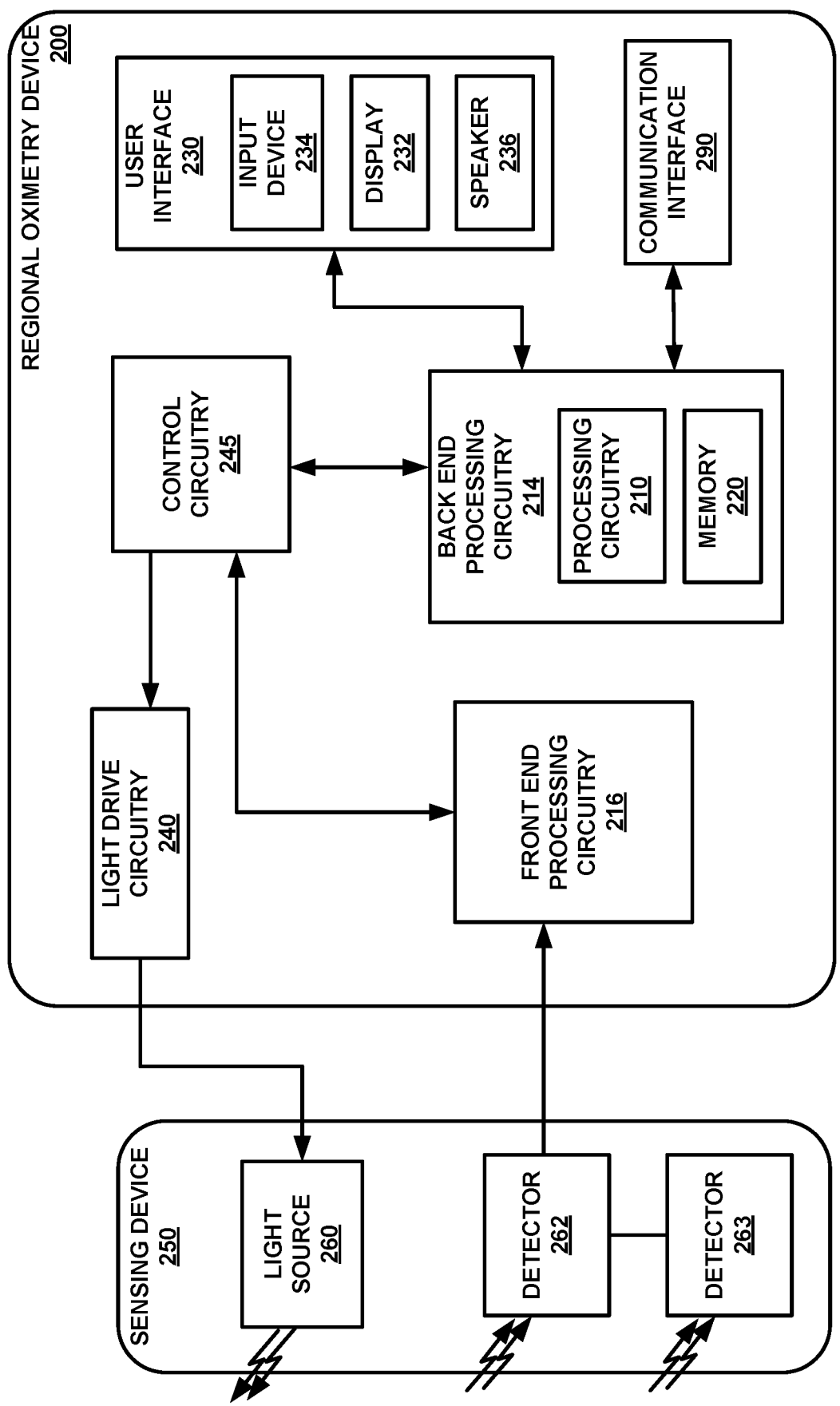
FIG. 2 is a conceptual block diagram illustrating an example regional oximetry device for monitoring the autoregulation status of a patient.

FIG. 2 is a conceptual block diagram illustrating an example regional oximetry device 200 for monitoring the autoregulation status of a patient. In the example shown in FIG. 2, regional oximetry device 200 is coupled to sensing device 250 and may be collectively referred to as a regional oximetry system, which each generate and process physiological signals of a subject. In some examples, sensing device 250 and regional oximetry device 200 may be part of an oximeter. As shown in FIG. 2, regional oximetry device 200 includes back-end processing circuitry 214, user interface 230, light drive circuitry 240, front-end processing circuitry 216, control circuitry 245, and communication interface 290. Regional oximetry device 200 may be communicatively coupled to sensing device 250. Regional oximetry device 200 is an example of regional oximetry device 100 shown in FIG. 1. In some examples, regional oximetry device 200 may also include a blood pressure sensor and/or a blood volume sensor (e.g., sensing devices 151 and 152 shown in FIG. 1).

In the example shown in FIG. 2, sensing device 250 includes light source 260, detector 262, and detector 263. In some examples, sensing device 250 may include more than two detectors. Light source 260 may be configured to emit photonic signals having two or more wavelengths of light (e.g., red and infrared (IR)) into a subject's tissue. For example, light source 260 may include a red light emitting light source and an IR light emitting light source, (e.g., red and IR light emitting diodes (LEDs)), for emitting light into the tissue of a subject to generate physiological signals. In some examples, the red wavelength may be between about 600 nm and about 700 nm, and the IR wavelength may be between about 800 nm and about 1000 nm. Other wavelengths of light may be used in other examples. Light source 260 may include any number of light sources with any suitable characteristics. In examples in which an array of sensors is used in place of sensing device 250, each sensing device may be configured to emit a single wavelength. For example, a first sensing device may emit only a red light while a second sensing device may emit only an IR light. In some examples, light source 260 may be configured to emit two or more wavelengths of near-infrared light (e.g., wavelengths between 600 nm and 1000 nm) into a subject's tissue. In some examples, light source 260 may be configured to emit four wavelengths of light (e.g., 724 nm, 770 nm, 810 nm, and 850 nm) into a subject's tissue. In some examples, the subject may be a medical patient.

As used herein, the term "light" may refer to energy produced by radiative sources and may include one or more of ultrasound, radio, microwave, millimeter wave, infrared, visible, ultraviolet, gamma ray or X-ray electromagnetic radiation. Light may also include any wavelength within the radio, microwave, infrared, visible, ultraviolet, or X-ray spectra, and that any suitable wavelength of electromagnetic radiation may be appropriate for use with the present techniques. Detectors 262 and 263 may be chosen to be specifically sensitive to the chosen targeted energy spectrum of light source 260.

In some examples, detectors 262 and 263 may be configured to detect the intensity of multiple wavelengths of near-infrared light. In some examples, detectors 262 and 263 may be configured to detect the intensity of light at the red and IR wavelengths. In some examples, an array of detectors may be used and each detector in the array may be configured to detect an intensity of a single wavelength. In operation, light may enter detector 262 after passing through the subject's tissue, including skin, bone, and other shallow tissue (e.g., non-cerebral tissue and shallow cerebral tissue). Light may enter detector 263 after passing through the subject's tissue, including skin, bone, other shallow tissue (e.g., non-cerebral tissue and shallow cerebral tissue), and deep tissue (e.g., deep cerebral tissue). Detectors 262 and 263 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detectors 262 and 263.

After converting the received light to an electrical signal, detectors 262 and 263 may send the detection signals to regional oximetry device 200, where the detection signals may be processed and physiological parameters may be determined (e.g., based on the absorption of the red and IR wavelengths in the subject's tissue at both detectors). In some examples, one or more of the detection signals may be preprocessed by sensing device 250 before being transmitted to regional oximetry device 200. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation," the entire content of which is incorporated herein by reference.

Control circuitry 245 may be coupled to light drive circuitry 240, front-end processing circuitry 216, and back-end processing circuitry 214, and may be configured to control the operation of these components. In some examples, control circuitry 245 may be configured to provide timing control signals to coordinate their operation. For example, light drive circuitry 240 may generate one or more light drive signals, which may be used to turn on and off light source 260, based on the timing control signals provided by control circuitry 245. Front-end processing circuitry 216 may use the timing control signals to operate synchronously with light drive circuitry 240. For example, front-end processing circuitry 216 may synchronize the operation of an analog-to-digital converter and a demultiplexer with the light drive signal based on the timing control signals. In addition, the back-end processing circuitry 214 may use the timing control signals to coordinate its operation with front-end processing circuitry 216.

Light drive circuitry 240, as discussed above, may be configured to generate a light drive signal that is provided to light source 260 of sensing device 250. The light drive signal may, for example, control the intensity of light source 260 and the timing of when light source 260 is turned on and off. In some examples, light drive circuitry 240 provides one or more light drive signals to light source 260. Where light source 260 is configured to emit two or more wavelengths of light, the light drive signal may be configured to control the operation of each wavelength of light. The light drive signal may comprise a single signal or may comprise multiple signals (e.g., one signal for each wavelength of light).

Front-end processing circuitry 216 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. The conditioned analog signals may be processed by an analog-to-digital converter of circuitry 216, which may convert the conditioned analog signals into digital signals. Front-end processing circuitry 216 may operate on the analog or digital form of the detector signals to separate out different components of the signals. Front-end processing circuitry 216 may also perform any suitable digital conditioning of the detector signals, such as low pass, high pass, band pass, notch, averaging, or any other suitable filtering, amplifying, performing an operation on the signal, performing any other suitable digital conditioning, or any combination thereof. Front-end processing circuitry 216 may decrease the number of samples in the digital detector signals. In some examples, front-end processing circuitry 216 may also remove dark or ambient contributions to the received signal.

Back-end processing circuitry 214 may include processing circuitry 210 and memory 220. Processing circuitry 210 may include an assembly of analog or digital electronic components and may be configured to execute software, which may include an operating system and one or more applications, as part of performing the functions described herein with respect to, e.g., processing circuitry 110. Processing circuitry 210 may receive and further process physiological signals received from front-end processing circuitry 216. For example, processing circuitry 210 may determine one or more physiological parameter values based on the received physiological signals. For example, processing circuitry 210 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof.

Processing circuitry 210 may perform any suitable signal processing of a signal, such as any suitable band-pass filtering, adaptive filtering, closed-loop filtering, any other suitable filtering, and/or any combination thereof. Processing circuitry 210 may also receive input signals from additional sources not shown. For example, processing circuitry 210 may receive an input signal containing information about treatments provided to the subject from user interface 230. Additional input signals may be used by processing circuitry 210 in any of the determinations or operations it performs in accordance with back-end processing circuitry 214 or regional oximetry device 200.

Processing circuitry 210 is an example of processing circuitry 110 and is configured to perform the techniques of this disclosure. For example, processing circuitry 210 is configured to receive signals indicative of physiological parameters. Processing circuitry 210 is also configured to determine correlation coefficient values and a metric for each bin of a plurality of bins, where each bin includes one or more correlation coefficient values. Processing circuitry 210 may be configured to determine a composite estimate based on the determined metrics. Processing circuitry 210 is also configured to determine an autoregulation status based on a composite estimate of a limit of autoregulation.

Memory 220 may include any suitable computer-readable media capable of storing information that can be interpreted by processing circuitry 210. In some examples, memory 220 may store bin parameters, correlation coefficient values, determined metrics, composite estimates, reference absorption curves, reference sets, determined values, such as blood oxygen saturation, pulse rate, blood pressure, fiducial point locations or characteristics, initialization parameters, any other determined values, or any combination thereof, in a memory device for later retrieval. Back-end processing circuitry 214 may be communicatively coupled with user interface 230 and communication interface 290.

User interface 230 may include input device 234, display 232, and speaker 236. User interface 230 is an example of user interface 130 shown in FIG. 1, and display 232 is an example of display 132 shown in FIG. 1. User interface 230 may include, for example, any suitable device such as one or more medical devices (e.g., a medical monitor that displays various physiological parameters, a medical alarm, or any other suitable medical device that either displays physiological parameters or uses the output of back-end processing 214 as an input), one or more display devices (e.g., monitor, personal digital assistant (PDA), mobile phone, tablet computer, clinician workstation, any other suitable display device, or any combination thereof), one or more audio devices, one or more memory devices, one or more printing devices, any other suitable output device, or any combination thereof.

Input device 234 may include any type of user input device such as a keyboard, a mouse, a touch screen, buttons, switches, a microphone, a joy stick, a touch pad, or any other suitable input device or combination of input devices. In other examples, input device 234 may be a pressure-sensitive or presence-sensitive display that is included as part of display 232. Input device 234 may also receive inputs to select a model number of sensing device 250, blood pressure sensor 250 (FIG. 2), or blood pressure processing equipment. In some examples, processing circuitry 210 may determine a width and/or separation distance between centers of adjacent bins for each plurality of bins based on user input received from input device 234. Thus, a user may be able to select, using input device 234, widths and/or separation distances for each plurality of bins.

Figure 3:
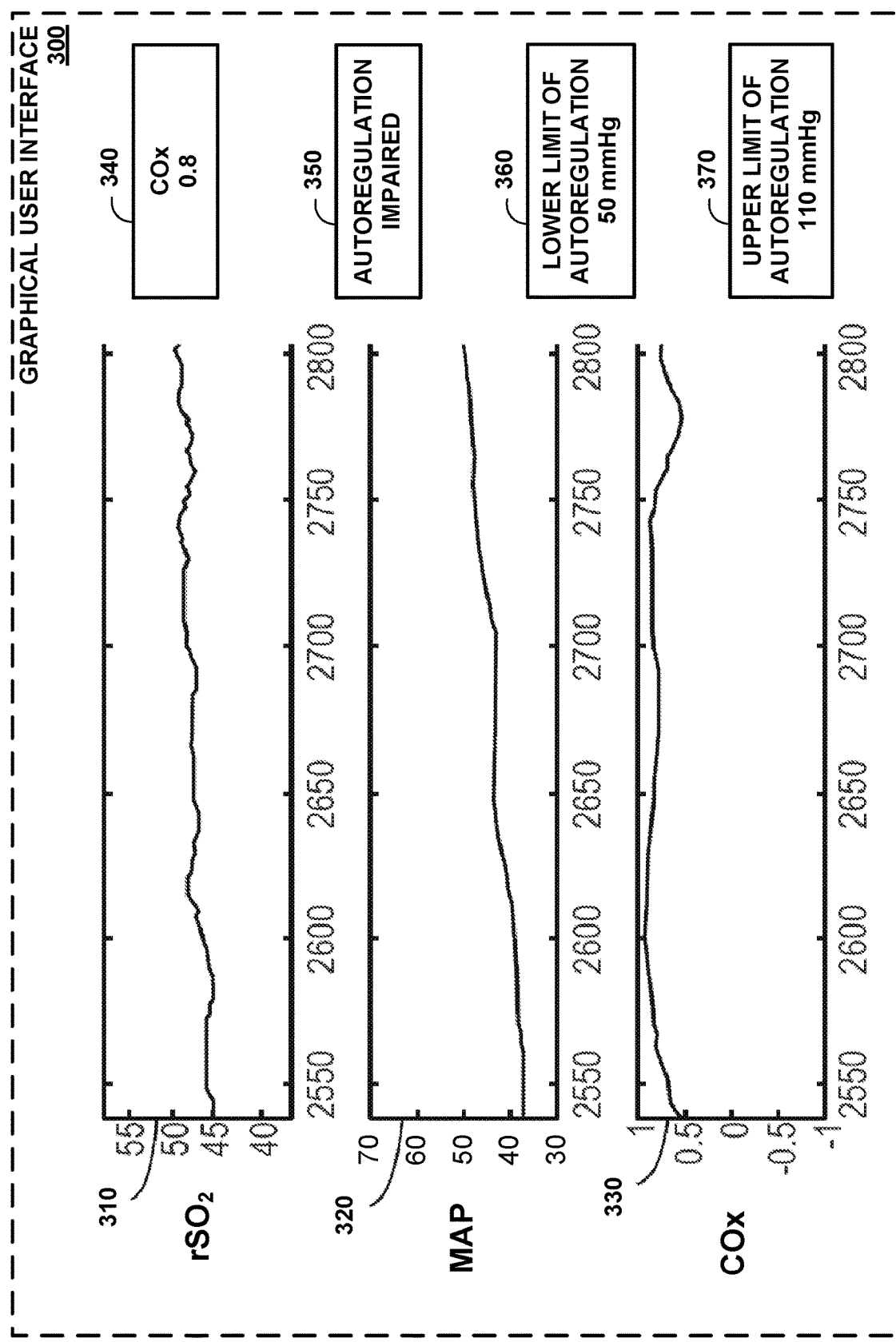
FIG. 3 illustrates an example graphical user interface including autoregulation information presented on a display.

In some examples, the subject may be a medical patient and display 232 may exhibit a list of values which may generally apply to the subject, such as, for example, an oxygen saturation signal indicator, a blood pressure signal indicator, a COx signal indicator, a COx value indicator, and/or an autoregulation status indicator. Display 232 may also be configured to present additional physiological parameter information. Graphical user interface 300 shown in FIG. 3 is an example of an interface that can be presented via display 232 of FIG. 2. Additionally, display 232 may present, for example, one or more estimates of a subject's regional oxygen saturation generated by regional oximetry device 200 (referred to as an "rSO$_2$" measurement). Display 232 may also present indications of the upper and lower limits of autoregulation. Speaker 236 within user interface 230 may provide an audible sound that may be used in various examples, such as for example, sounding an audible alarm in the event that a patient's physiological parameters are not within a predefined normal range.

Communication interface 290 may enable regional oximetry device 200 to exchange information with external devices. Communication interface 290 may include any suitable hardware, software, or both, which may allow regional oximetry device 200 to communicate with electronic circuitry, a device, a network, a server or other workstations, a display, or any combination thereof. For example, regional oximetry device 200 may receive MAP values and/or oxygen saturation values from an external device via communication interface 290.

The components of regional oximetry device 200 that are shown and described as separate components are shown and described as such for illustrative purposes only. In some examples the functionality of some of the components may be combined in a single component. For example, the functionality of front end processing circuitry 216 and back-end processing circuitry 214 may be combined in a single processor system. Additionally, in some examples the functionality of some of the components of regional oximetry device 200 shown and described herein may be divided over multiple components. For example, some or all of the functionality of control circuitry 245 may be performed in front end processing circuitry 216, in back-end processing circuitry 214, or both. In other examples, the functionality of one or more of the components may be performed in a different order or may not be required. In some examples, all of the components of regional oximetry device 200 can be realized in processor circuitry.

FIG. 3 illustrates an example graphical user interface 300 including autoregulation information presented on a display. FIG. 3 is an example of a presentation by processing circuitry 110 on display 132 shown in FIG. 1 or by processing circuitry 210 on display 232 shown in FIG. 2. Graphical user interface 300 may be configured to display various information related to blood pressure, oxygen saturation, the COx index, limits of autoregulation, and/or autoregulation status. As shown, graphical user interface 300 may include oxygen saturation signal indicator 310, blood pressure signal indicator 320, and COx signal indicator 330. Graphical user interface 300 may include COx value indicator 340, autoregulation status indicator 350, and limit of autoregulation indicators 360 and 370.

Blood pressure signal indicator 320 may present a set of MAP values determined by processing circuitry 110 of regional oximetry device 100. In some examples, blood pressure signal indicator 320 may present MAP values as discrete points over time or in a table. Blood pressure signal indicator 320 may also present MAP values as a moving average or waveform of discrete points. Blood pressure signal indicator 320 may present MAP values as a single value (e.g., a number) representing a current MAP value. Oxygen saturation signal indicator 310 and COx signal indicator 330 may also present rSO2 values and COx values, respectively, as discrete points, in a table, as a moving average, as a waveform, and/or as a single value.

COx signal indicator 330 may present a set of correlation coefficient values determined by processing circuitry 110. Processing circuitry 110 may determine the correlation coefficient values as a function of the oxygen saturation values presented in oxygen saturation signal indicator 310 and the MAP values presented in blood pressure signal indicator 320. In some examples, a COx value at or near one (unity) indicates the autoregulation status of a patient is impaired, as shown in autoregulation status indicator 350.

Figure 5:
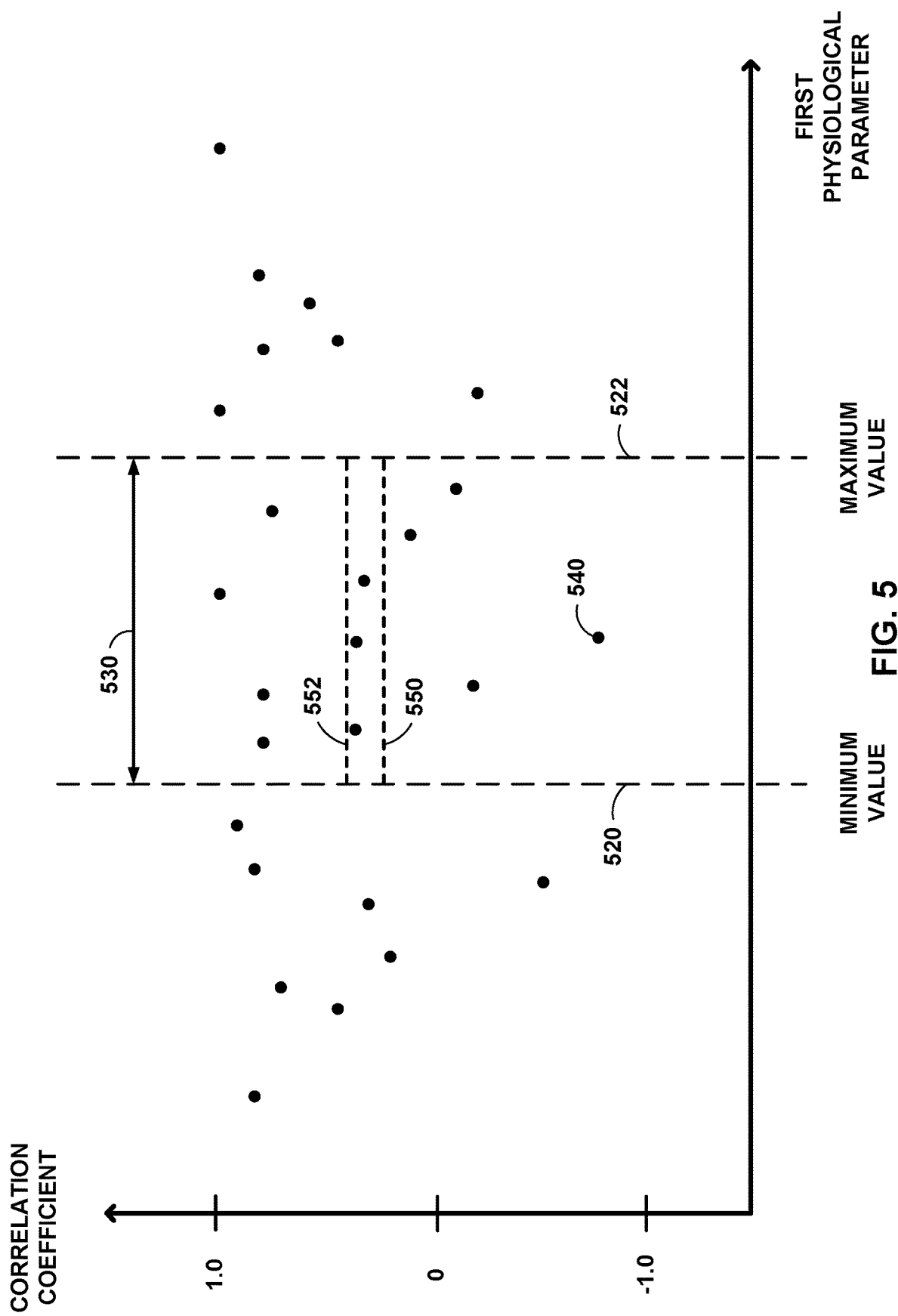
FIG. 5 is an example graph illustrating the binning of correlation coefficient values.
Figure 6A:
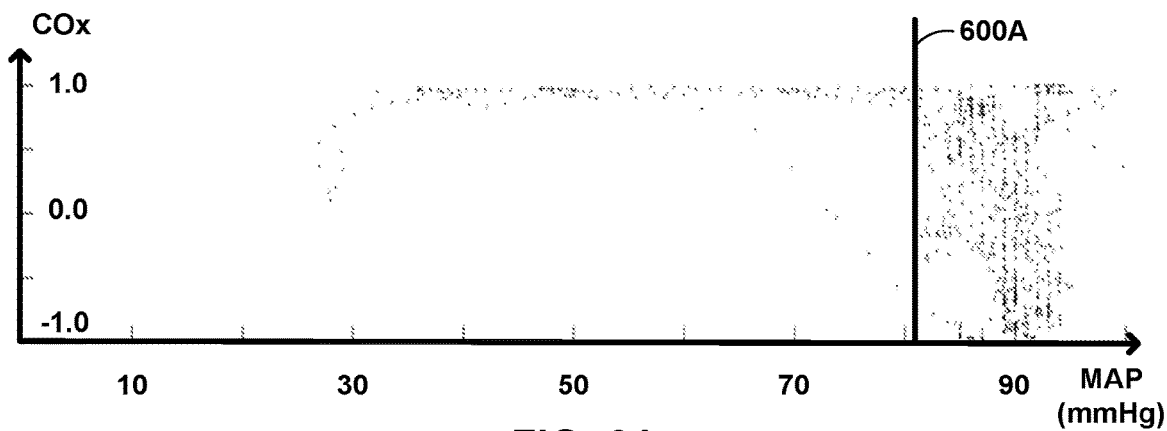
FIGS. 6A-6C illustrate two example binning strategies for porcine data.

Processing circuitry 110 may determine a set of correlation coefficient values and associated values of a first physiological parameter using the values presented in indicators 310, 320, and/or 330. Processing circuitry 110 may determine a COx value and the associated value of the first physiological parameter (e.g., MAP or rSO$_2$) for a particular time (e.g., 2,550 seconds in the graphs of indicators 320 and 330). This COx value may be an "unbinned COx value," and processing circuitry 110 can plot the unbinned COx value along with the associated MAP value. FIGS. 5 and 6A depict unbinned correlation coefficient values plotted with the associated MAP values.

Processing circuitry 110 may be configured to determine and store, in memory 120, a set of correlation coefficient values, e.g., as a two-dimensional array. Each row of the array may be a separate entry (e.g., a COx value and an associated MAP value). The first column of the array may be the MAP values presented in blood pressure signal indicator 320. The second column of the array may be the COx values presented in COx signal indicator 330. Processing circuitry 110 can plot each entry of the array as shown in FIGS. 5 and 6A, with the MAP value being the value along the horizontal axis and the COx value being the value along the vertical axis.

COx value indicator 340 shows a COx value of 0.8, which may result in a determination by processing circuitry 110 that the autoregulation status of the patient is impaired. Processing circuitry 110 may be configured to present, as the COx value in COx value indicator 340, the most recently determined COx value or a moving average of recently determined COx values. In order to determine the autoregulation status of a patient for presentation in autoregulation status indicator 350, processing circuitry 110 may determine whether the most recent MAP value shown in blood pressure signal indicator 320 is between the limits of autoregulation presented in limit of autoregulation indicators 360 and 370.

Processing circuitry 110 may present limit of autoregulation indicators 360 and/or 370 in terms of blood pressure, for example, mmHg. Processing circuitry 110 can determine the limits of cerebral autoregulation (LLA and ULA) for presentation in indicators 360 and 370 based on a relationship between the blood pressure of a patient and another physiological parameter of the patient. For example, indicator 360 may be highlighted when the LLA has been exceeded or indicator 360 may be highlighted when the ULA has been exceeded. In other examples, a single indicator may present the type of limit that has been exceed by the MAP value. If the LLA or ULA change, processing circuitry 110 may control user interface 300 to change the value of the LLA or ULA in accordance with any change to that respective value.

Processing circuitry 110 may determine a composite estimate of a lower limit of autoregulation presented in indicator 360 and/or a composite estimate of an upper limit of autoregulation presented in indicator 370. Processing circuitry 110 may be configured to generate a notification in response to determining that the MAP value is less than or equal to the composite average of the lower limit of autoregulation. Processing circuitry 110 may output the notification in autoregulation status indicator 350 as text, color, blinking, and/or any other suitable visible or audible manner.

Figure 4:
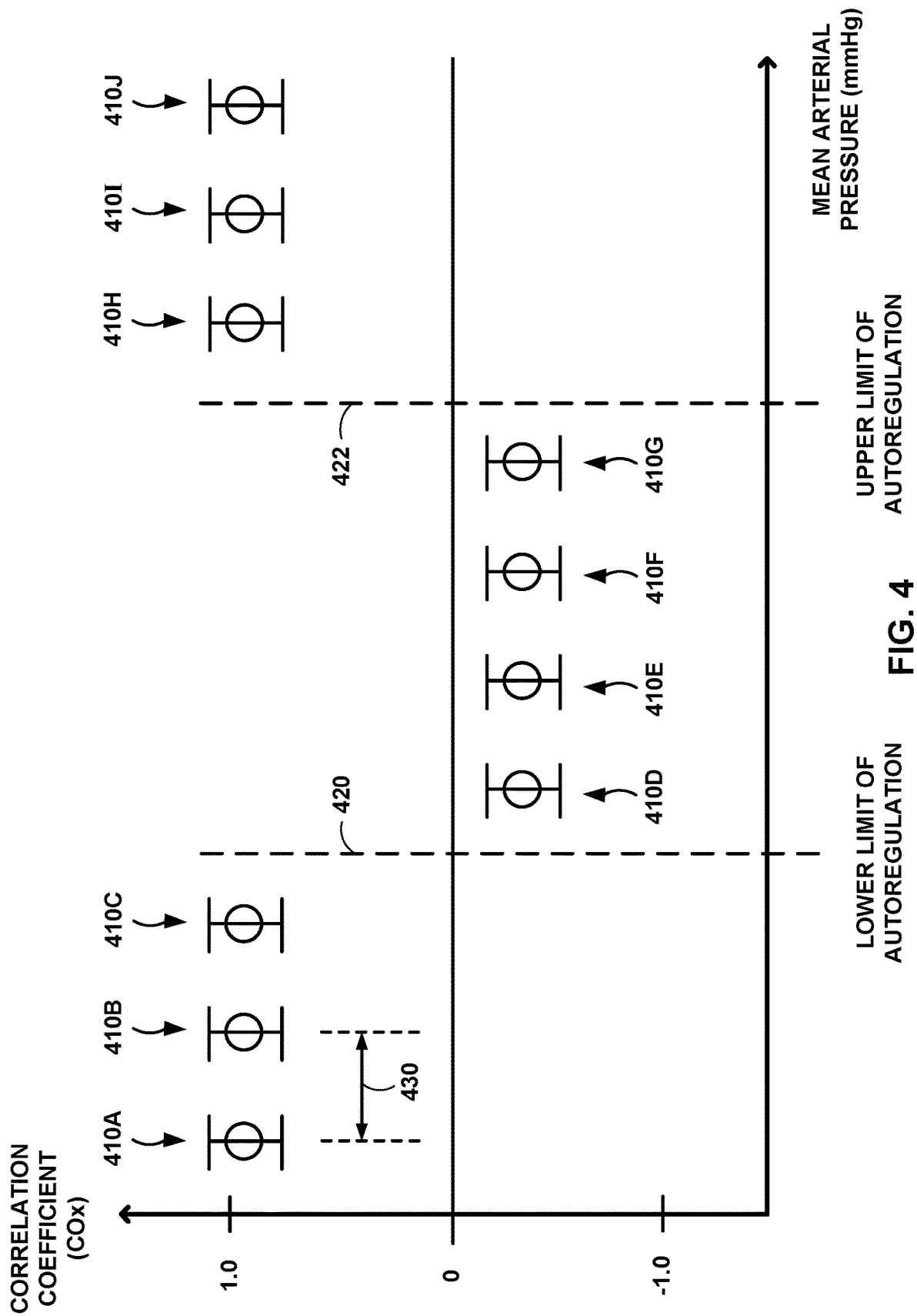
FIG. 4 is an example graph illustrating metrics for bins of correlation coefficient values versus mean arterial pressure.

FIG. 4 is an example graph illustrating metrics for bins of correlation coefficient values versus mean arterial pressure. Each of symbols 410A-410J depicts the metric (e.g., an average correlation coefficient value) of each bin (e.g., at the center of a circle) along with an error bar. In some examples, the error bar represents the largest and smallest values of the correlation coefficient values in the respective bin. In some examples, the error bar represents the standard deviation and/or percentiles of the correlation coefficient values in the bin. Although FIGS. 4-9 are described with respect to processing circuitry 110 of regional oximetry device 100 (FIG. 1), in other examples, processing circuitry 210, 214, and/or 216 (FIG. 2), alone or in combination with processing circuitry 110, may perform any part of the techniques of FIGS. 4-9. The graph of FIG. 4 depicts COx values plotted against MAP values, but processing circuitry 110 can use other physiological parameters to determine a limit of autoregulation. For example, processing circuitry 110 may use brain-cerebral perfusion pressure (CPP) and cerebral blood flow (CBF) to determine the Mx measure.

A strong positive correlation may exist between MAP and $rSO_2$ in regions of autoregulatory impairment, hence the COx values may tend to a value of unity, as shown by symbols 410A-410C and 410H-410J. Regions of intact autoregulation, however, may produce no correlation between $rSO_2$ and changes in MAP and hence the COx values may be near or below zero in the intact region, as shown by symbols 410D-410G. In this ideal case, a step change shown by symbols 410A-410J may occur when transitioning from intact to impaired regions at LLA 420 or ULA 422. In practice, however, the binned data may be generally noisy and processing circuitry 110 may use a COx threshold level somewhere between zero and positive one to differentiate the correlating and non-correlating portions of the plot. For example, processing circuitry 110 may use a threshold level of 0.0, 0.1, 0.2, 0.3, 0.4, or 0.5 to determine a limit of autoregulation.

The bins associated with symbols 410A-410J may be part of a first plurality of bins, where each of the bins associated with symbols 410A-410J has a width and a separation distance 430 between centers of adjacent bins. Each of symbols 410A-410J is depicted to include an upper horizontal line, a lower horizontal line, and a middle circle. The upper horizontal line may represent the highest COx value in the bin, and the lower horizontal line may represent the lowest COx value in the bin. In some examples, the horizontal lines indicate standard deviations and/or percentiles of the correlation coefficient values in a bin. The center of the circle may represent the value of the metric (e.g., mean, weighted average, or median) for the bin. Processing circuitry 110 may be configured to remove, exclude, or not use outlier values of the correlation coefficient values to determine the highest COx value, the lowest COx value, and/or the value of the metric.

Processing circuitry 110 can determine or derive a COx value from the correlation between $rSO_2$ and MAP. Processing circuitry 110 can determine the COx value as the Pearson coefficient relating to the regression line fit between $rSO_2$ and MAP over a 300-second window. Processing circuitry 110 can use the COx method to produce a picture of the patient's blood-pressure-dependent autoregulation status. The COx plot shown in FIG. 4 may exhibit a drop in typical values when transitioning from pressures below the LLA (e.g., limit 420) to the intact region of autoregulation and similarly, at higher pressures, exhibits a step increase when transitioning from the intact region of autoregulation to pressures above the ULA (e.g., limit 422). Processing circuitry 110 may plot the data by binning the COx values in non-overlapping bins at five mmHg intervals (e.g., separation distances). In addition, each bin may be five mmHg wide. FIG. 4 illustrates plotting the mean of the correlation coefficient values in each bin with an associated error bar, as shown in FIG. 4.

FIG. 5 is an example graph illustrating the binning of correlation coefficient values. The graph of FIG. 5 depicts twenty-six determined correlation coefficient values, but in other examples there may be more or fewer correlation coefficient values determined. For example, processing circuitry 110 may be configured to determine one or more correlation coefficient values every second. Processing circuitry 110 may use a window of three hundred seconds such that there are hundreds of correlation coefficient values for the determination of metrics of a plurality of bins.

The graph of FIG. 5 includes a single bin with width 530. Width 530 is defined by the difference between maximum value 522 and minimum value 520. Width 530 is defined in terms of the first physiological parameter, which may be MAP, $rSO_2$, HVS, BVS, etc. If processing circuitry 110 uses MAP as the first physiological parameter, processing circuitry 110 can determine width 530 in terms of mmHg, such as one mmHg, two mmHg, three mmHg, four mmHg, five mmHg, and/or any other suitable width. Although FIG. 5 depicts only one bin, processing circuitry 110 may be configured to determine a plurality of bins across a range of the first physiological parameter.

The graph of FIG. 5 depicts eleven correlation coefficient values in the bin bounded by maximum value 522 and minimum value 520. Processing circuitry 110 may be configured to determine a metric for the bin at least in part by determining the metric of the correlation coefficient values associated with values of the first physiological parameter (e.g., MAP) in a range of greater than minimum value 520 and less than maximum value 522 (e.g., the eleven correlation coefficient values positioned between values 520 and 522). In some examples, processing circuitry 110 determines a metric for the bin by determining mean 550 of the eleven correlation coefficient values.

Additionally or alternatively, processing circuitry 110 can determine a metric for the bin by excluding outlier correlation coefficients (e.g., outlier correlation coefficient 540) and determining a mean of the remaining coefficient values (e.g., determining mean 552 of the remaining ten correlation coefficient values). Processing circuitry 110 can determine mean 550 and a standard deviation of the eleven correlation coefficient values for the bin. Processing circuitry 110 can then determine that correlation coefficient 540 is greater than three times the standard deviation from mean 550. For example, processing circuitry may determine that mean 550 is equal to 0.2 and that the standard deviation is equal to 0.3. In response to determining that correlation coefficient 540 is equal to −0.8, processing circuitry 110 determines that correlation coefficient 540 is greater than three times the standard deviation from mean 550. In some examples, the determination of an outlier may be based on a different factor, such as two times or four times the standard deviation. Processing circuitry 110 then determines mean 552, excluding correlation coefficient 540, for the bin. Thus, processing circuitry 110 may exclude any outliers in a bin before calculating the metric for the bin in order to mitigate against noisy values.

Mean 552 may be a more accurate estimate of the mean correlation coefficient between values 520 and 522 because correlation coefficient 540 may be an outlier caused by temporary patient events such as catherization of the patient, probe (e.g., sensor) movement relative to the patient, or line flushing, and should be disregarded. Excluding correlation coefficient 540 from the determination of mean 552 may result in a more accurate determination of the metric for the bin and, consequently, a more accurate determination of an estimate of a limit of autoregulation and an autoregulation status.

$$\text{Weighted average} = \frac{1}{\sum_{i=1}^{N} A_i} \sum_{i=1}^{N} (A_i \times COx_i) \quad (2)$$

In some examples, processing circuitry 110 may determine a metric for a bin that is a weighted average (e.g., a weighted mean) of the correlation coefficient values in the bin. Processing circuitry 110 may use Equation (2) to determine a weighted average using a weighting factor for each correlation coefficient. In some examples, processing circuitry 110 may determine a weighting factor ($A_i$ in Equations (2)-(4)) for each correlation coefficient, where each weighting factor may be based on a characteristic of the respective correlation coefficient.

For example, the characteristic can be the distance from the center of the bin to the value of the first physiological parameter associated with the correlation coefficient ($MAP_i$), as shown in Equations (3) and (4). According to Equations (3) and (4), correlation coefficient values closer to the center of the bin ($MAP_{center}$) are weighted higher than correlation coefficient values farther from the center of the bin. Processing circuitry 110 may use Equation (3) to determine a weighting factor based on a linear (e.g., triangular) function, where the weighting factor is equal to one for a correlation coefficient positioned at the center of a bin and equal to zero for a correlation coefficient positioned at the edge of a bin. Processing circuitry 110 may use Equation (4) to determine a weighting factor based on a Gaussian distribution function.

$$A_i = \frac{|MAP_i - MAP_{center}|}{\text{bin width}} \quad (3)$$

$$A_i = \frac{1}{\sigma\sqrt{2\pi}} e^{-\frac{(MAP_i - MAP_{center})^2}{2\sigma^2}} \quad (4)$$

Processing circuitry 110 can alternatively or additionally determine the weighting factors on the age of the correlation coefficient, such that processing circuitry 110 assigns higher weighting factors to more recent correlation coefficient values, as compared to less recent correlation coefficient values. Processing circuitry 110 can also determine the weighting factor based on a signal quality metric, such that processing circuitry 110 assigns higher weighting factors to correlation coefficient values based on higher quality signals, as compared to correlation coefficient values based on lower quality signals. Processing circuitry 110 may determine the quality of a correlation coefficient based on the characteristics of signals received by processing circuitry 110 from sensing devices 150-152 and sensing circuitry 140-142. These characteristics include signal strength, variability, noise level, and/or any other signal characteristics that indicate the quality of the signal, such as a signal-to-noise ratio. Drop outs in the signals (e.g., time periods without any data) received by processing circuitry 110 can be indicators of poor quality in the respective signal. Processing circuitry 110 may be configured to compare a correlation coefficient value to previously determined correlation coefficient values in a range of similar blood pressures to determine if the correlation coefficient value is an outlier.

Processing circuitry 110 may use weighting factors to improve the metrics determined for each bin. For example, processing circuitry 110 may use weighting factors to filter out unreliable correlation coefficient values or less representative correlation coefficient values. Further, processing circuitry 110 may use weighting factors to determine a metric that is representative of the center of the bin, rather than the edges of the bin.

Figure 6B:
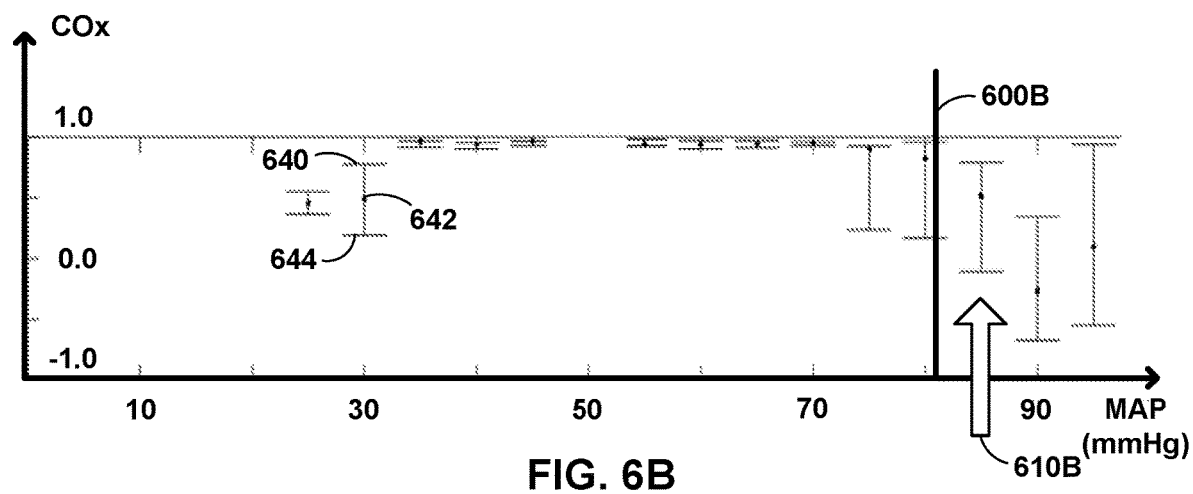
Figure 6C:
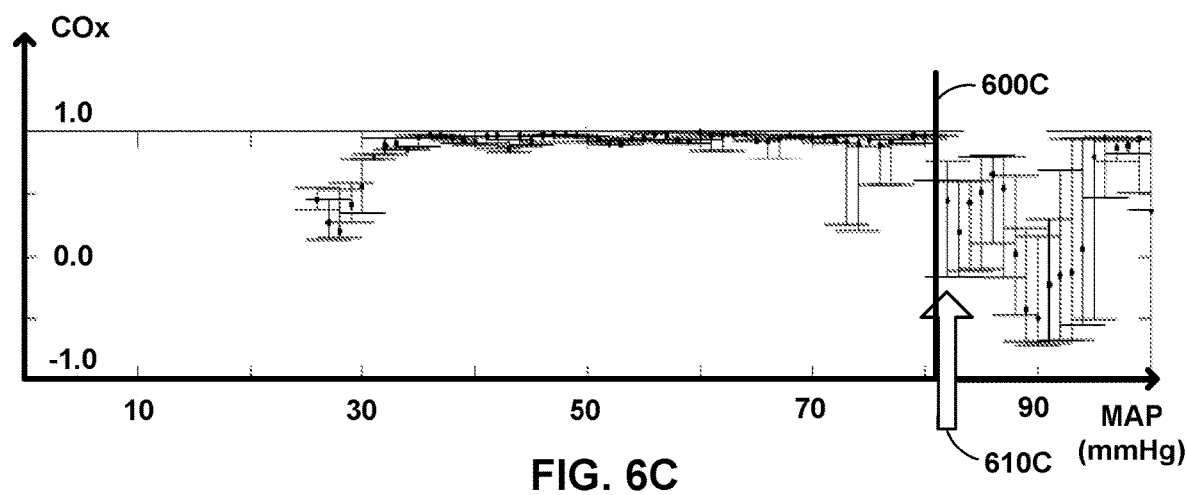
Figure 7A:
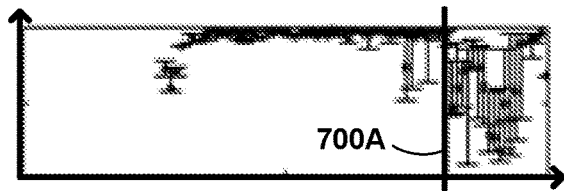
FIGS. 7A-7G illustrate seven example binning strategies for porcine data.
Figure 7B:
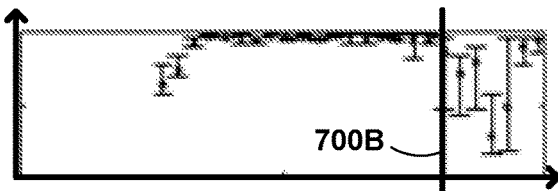
Figure 7C:
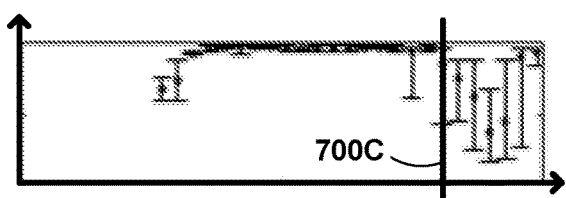
Figure 7D:
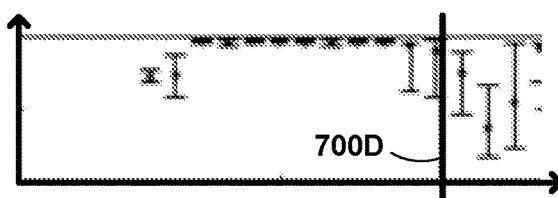
Figure 7E:
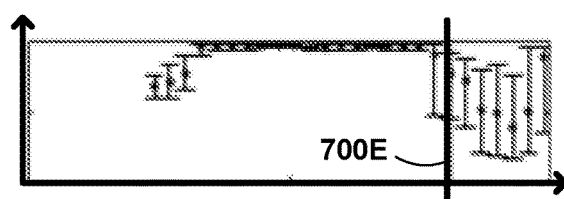
Figure 7F:
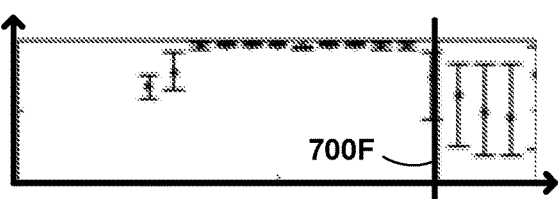
Figure 7G:
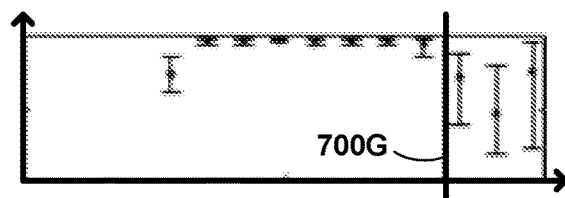

FIGS. 6A-6C illustrate two example binning strategies for porcine data. FIG. 6A illustrates unbinned correlation coefficient values. Lower limits of autoregulation 600A, 600B, and 600C represent a visual estimate of the separation between the intact region of autoregulation where COx values vary from −1 to +1 and the impaired region of autoregulation where COx values are often only at or near+1. Lower limits of autoregulation 600A, 600B, and 600C are near a MAP value of 82 mmHg.

FIG. 6B illustrates a first plurality of bins having a first width and a first separation distance between centers of adjacent bins. FIG. 6C illustrates a second plurality of bins having a second width and a second separation distance between centers of adjacent bins. In some examples, the first width equals five mmHg and the first separation distance equals five mmHg for FIG. 6B, and the second width equals two mmHg and the second separation distance equals one mmHg for FIG. 6C.

Processing circuitry 110 may be configured to determine a first estimate of the lower limit of autoregulation based on the metric of the correlation coefficient values for the first plurality of bins depicted in FIG. 6B. Processing circuitry 110 may determine the first estimate of the lower limit of autoregulation as illustrated by the bin at which arrow 610B is pointing, i.e., the bin centered at 85 mmHg. Processing circuitry 110 may determine the first estimate of the lower limit of autoregulation by moving from left to right, from impaired to intact, to find the first bin at which the metric is less than a threshold level. For example, the metric for the bins shown in FIG. 6B does not drop significantly until the bin centered at 85 mmHg. Processing circuitry 110 may use an algorithm (e.g., finding the lowest bin having a metric below a threshold level) to determine the lower limit of autoregulation. Using a separation distance of five mmHg in FIG. 6B, processing circuitry 110 may not be able to determine the first estimate of the lower limit of autoregulation to a resolution finer than five mmHg. Thus, processing circuitry 110 may only be able to determine the first estimate of the lower limit of autoregulation at 80 mmHg or 85 mmHg, and not at 81, 82, 83, or 84 mmHg. There may be significantly more variation between the metrics of adjacent bins when using a larger separation distance, as compared to the variation between the metrics of adjacent bins when using a smaller separation distance.

Processing circuitry 110 may be configured to determine a second estimate of the lower limit of autoregulation based on the metric of the correlation coefficient values for the second plurality of bins depicted in FIG. 6C, which is a more fine-grained approach than the first plurality of bins shown in FIG. 6B. Processing circuitry 110 may determine the second estimate of the lower limit of autoregulation as illustrated by the bin at which arrow 610C is pointing, i.e., the bin centered at 82 mmHg. Processing circuitry 110 may determine the second estimate of the lower limit of autoregulation by moving from left to right, from impaired to intact, to find the first bin at which the metric has dropped below a threshold level (e.g., jumped downwards). Using a separation distance of one mmHg in FIG. 6C, processing circuitry 110 may be able to determine the first estimate of the lower limit of autoregulation to a resolution of one mmHg. Thus, processing circuitry 110 may be able to determine the first estimate of the lower limit of autoregulation at 80, 81, 82, 83, 84, or 85 mmHg based on the metric for the bins centered at each MAP value. Using a smaller separation distance results in more bins on either side of lower limit of autoregulation 600C and much better resolution than FIG. 6B.

Processing circuitry 110 may determine a more accurate estimate of a limit of autoregulation (e.g., much better detection) based on the second plurality of bins, where each bin has a smaller width and a smaller separation distance than the first plurality of bins shown in FIG. 6B. The smaller width of the second plurality of bins may result in better resolution of the metrics determined by processing circuitry 110.

Processing circuitry 110 may be further configured to determine a composite estimate of the lower limit of autoregulation based on the first estimate and the second estimate. Processing circuitry 110 may determine composite estimate based on a mean, median, average, and/or weighted average of the first estimate and the second estimate (e.g., 83.5 mmHg). The use of first and second estimates is an example, and in other examples, processing circuitry 110 may determine a composite estimate based on more than two estimates. Processing circuitry 110 may then be configured to determine an autoregulation status of a patient based on the composite estimate of the limit of autoregulation by determining whether the most recent MAP value for the patient is less than or equal to the composite estimate. Processing circuitry 110 may simultaneously use several different combinations of bin locations and bin widths to determine an estimate of a limit of autoregulation. Processing circuitry 110 may determine an average of the resulting estimates to produce a single value (e.g., a composite estimate), and processing circuitry 110 may use the level of agreement between values as a confidence measure.

FIGS. 7A-7G illustrates seven example binning strategies for porcine data. Each graph of FIGS. 7A-7G depicts a plurality of bins determined by processing circuitry 110. The text above each graph of FIGS. 7A-7G shows the width and separation distance between centers of adjacent bins for each plurality of bins. In general, processing circuitry 110 will determine a more accurate estimate of a limit of autoregulation using a smaller width and/or smaller separation distance, although greater accuracy is sometimes possible with larger widths and/or larger separation distances. By using a smaller separation distance, processing circuitry 110 can determine, with finer granularity, greater resolution, and greater precision, a step-down or step-up in metrics that occurs near limits of autoregulation.

By using a smaller separation distance, processing circuitry 110 may consume more processing resources, as compared to using a larger separation distance. In addition, processing circuitry 110 may use more processing resources to determine metrics for two or more pluralities of bins than to determine metrics for only one plurality of bins. However, processing circuitry 110 may have sufficient processing resources available to determine metrics for many pluralities of bins having relatively small separation distances.

In some examples, processing circuitry 110 is configured to determine a metric for a first plurality of bins having a first separation distance between centers of adjacent bins. Processing circuitry 110 may also be configured to determine a metric for a second plurality of bins having a second separation distance between centers of adjacent bins. In some examples, the first and second pluralities of bins may have the same widths. Thus, processing circuitry 110 may use different values for one or more bin parameter for each pluralities of bins and use the same values for other bin parameter(s) for the pluralities of bins. The bin parameters include one or more of width, separation distance between centers of adjacent bins, algorithms used to determine weighting factors, maximum age of correlation coefficient values, maximum number of correlation coefficient values, and/or any other suitable bin parameters.

In some examples, processing circuitry 110 determines two or more estimates of a limit of autoregulation that are not equal. Processing circuitry 110 may determine a first estimate of the limit of autoregulation based on a first plurality of bins and a second estimate of the limit of autoregulation based on a second plurality of bins. Although a plurality of bins with a smaller width and/or smaller separation distance may generally result in a more accurate estimate, a plurality of bins with a larger width and/or larger separation distance may sometimes result in a more accurate estimate. Thus, if processing circuitry 110 uses two or more pluralities of bins, rather than only one plurality of bins, the resulting composite estimate may generally be a more accurate estimate of the limit of autoregulation, as compared to an estimate based on only one plurality of bins. Moreover, processing circuitry 110 may more quickly determine and report changes in a limit of autoregulation, relative to when the changes actually occur in a patient, using two or more pluralities of bins.

Figure 8:
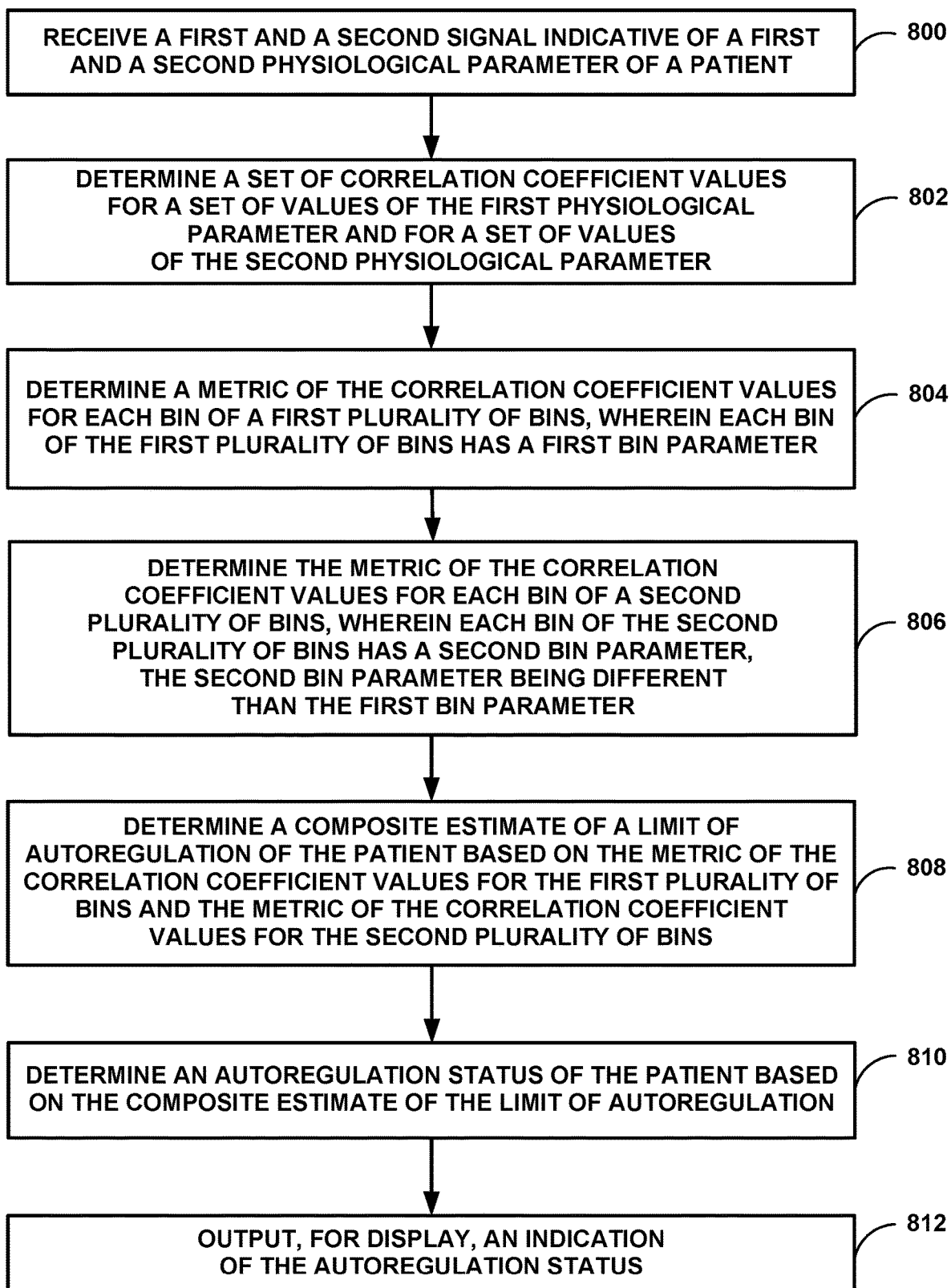
FIGS. 8 and 9 are flow diagrams illustrating example techniques for determining changes in autoregulation, in accordance with some examples of this disclosure.
Figure 9:
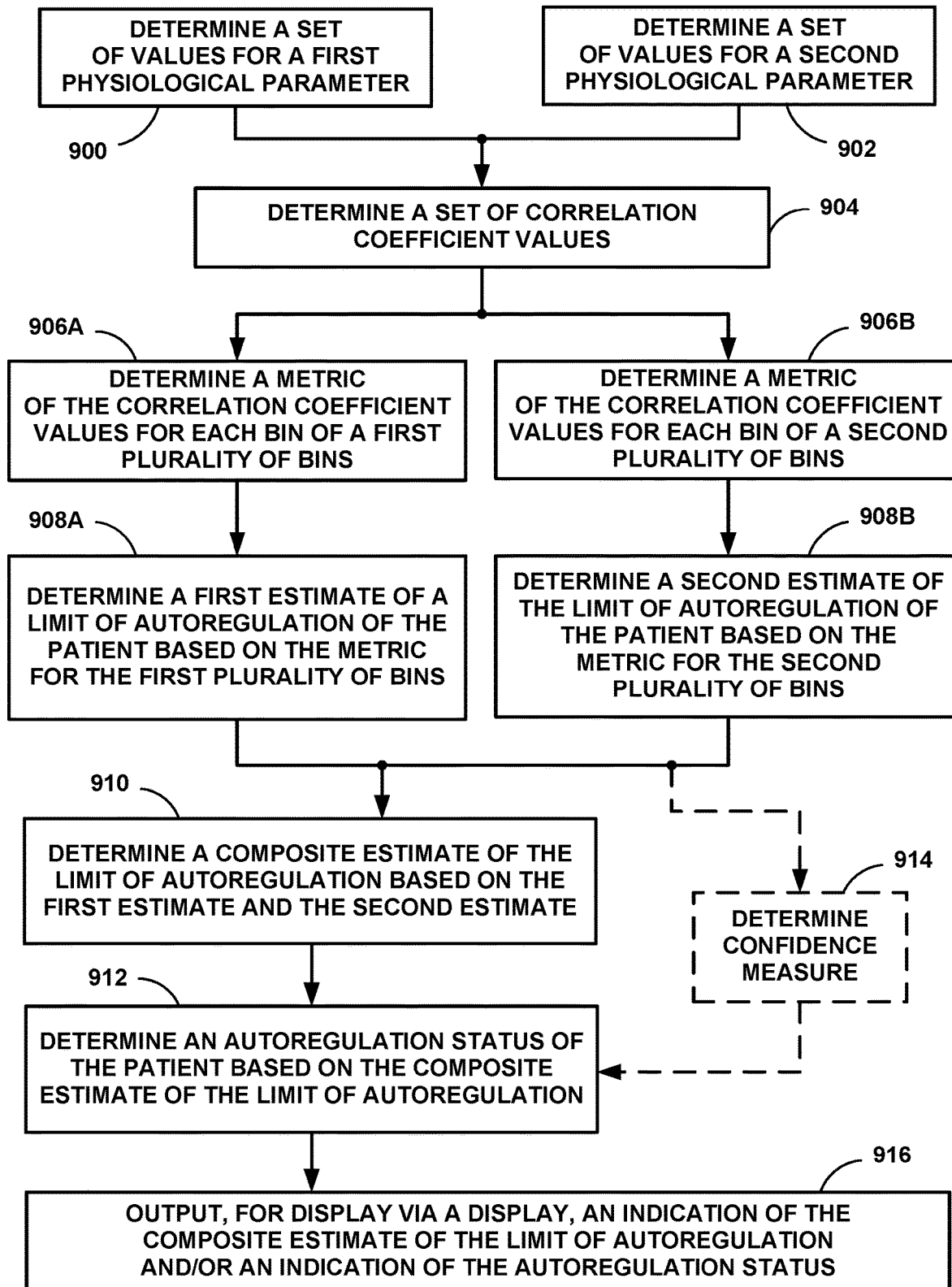

FIGS. 8 and 9 are flow diagrams illustrating example techniques for determining changes in autoregulation, in accordance with some examples of this disclosure. Although FIGS. 8 and 9 are described with respect to processing circuitry 110 of regional oximetry device 100 (FIG. 1), in other examples, processing circuitry 210, 214, and/or 216 (FIG. 2), alone or in combination with processing circuitry 110, may perform any part of the techniques of FIGS. 8 and 9.

In the example of FIG. 8, processing circuitry 110 receives a first signal indicative of a first physiological parameter of a patient and a second signal indicative of a second physiological parameter of the patient (800). In some examples, processing circuitry 110 receives signals directly from sensing devices 150-152. Additionally or alternatively, processing circuitry 110 receives signals from sensing circuitry 140-142, where sensing circuitry 140-142 may pre-process the physiological signals before delivering the signals to processing circuitry 110.

In the example of FIG. 8, processing circuitry 110 determines a set of correlation coefficient values for a set of values of the first physiological parameter and for a set of values of the second physiological parameter (802). Processing circuitry 110 may determine each correlation coefficient, for example, as a Pearson's coefficient for the two physiological parameters. Each correlation coefficient value may indicate the linear correlation between the two physiological parameters at a particular time or over a particular window of time. In some examples, processing circuitry 110 may determine the linear correlation between the two physiological parameters over a window of five seconds or ten seconds.

In the example of FIG. 8, processing circuitry 110 determines a metric of the correlation coefficient values for each bin of a first plurality of bins, wherein each bin of the first plurality of bins has a first bin parameter defined in terms of the first physiological parameter (804). Processing circuitry 110 then determines a metric of the correlation coefficient values for each bin of a second plurality of bins, wherein each bin of the second plurality of bins has a second bin parameter defined in terms of the first physiological parameter that is different than the first bin parameter (806). The bin parameter can include one or more of the width of each bin, the separation distance between adjacent bins, and/or the algorithms used to determine weighting factors for the correlation coefficient values in each bin. In some examples, processing circuitry 110 may determine the metric of the correlation coefficient values for only one plurality of bins, where the plurality of bins has a width of less than five mmHg and a separation distance of less than five mmHg to provide for better resolution.

Processing circuitry 110 may use a mean, median, weighted average, or any other metric as the metric for each of the bins. If the first physiological parameter is mean arterial pressure, then the widths for each plurality of bins may be one mmHg, two mmHg, three mmHg, four mmHg, five mmHg, or any other suitable width. Processing circuitry 110 may optimize the width of the bins for the detection of a limit of autoregulation by changing the bin parameters including the width of the bins or the separation distance between bin centers. For example, processing circuitry 110 may use ten mmHg wide bins, separated by five mmHg which may be more robust to noise in individual bins. Processing circuitry 110 may use a smaller separation such as one mmHg with a width of two mmHg to find a more granular estimate of the limit of autoregulation.

In the example of FIG. 8, processing circuitry 110 determines a composite estimate of a limit of autoregulation of the patient based on the metric of the correlation coefficient values for the first plurality of bins and the metric of the correlation coefficient values for the second plurality of bins (808). Processing circuitry 110 may first determine an estimate of the limit of autoregulation for each plurality of bins and then determine the composite estimate based on the estimates for each of the plurality of bins. Processing circuitry 110 may determine the composite estimate based on an average of the estimates for each plurality of bins. Alternatively or additionally, processing circuitry 110 can determine the composite estimate based on previous estimates, as discussed with respect to FIG. 9.

In the example of FIG. 8, processing circuitry 110 determines an autoregulation status of the patient based on the composite estimate of the limit of autoregulation (810). Processing circuitry 110 can determine the autoregulation status at least in part by determining whether the current mean arterial pressure value of the patient is greater than the composite estimate of the lower limit of autoregulation and/or less than the composite estimate of the upper limit of autoregulation. Processing circuitry 110 outputs an indication of the autoregulation status for display via display 132 (812). Processing circuitry 110 can cause display 132 to present one or more of the indicators 310, 320, 330, 340, 350, 360, and 370. For example, processing circuitry 110 can cause display 132 to present autoregulation status indicator 350, which may include text or a color representative of an impaired or intact autoregulation status.

Processing circuitry 110 may also use the techniques of this disclosure to determine the composite estimate based on HVx values, PRx values, and/or Mx values, rather than just COx values, using the binning techniques described herein. For example, in step 802, processing circuitry 110 can determine a set of HVx values, PRx values, and/or Mx values and then determine a metric of the HVx values, PRx values, and/or Mx values for a plurality of bins. Processing circuitry 110 may use the techniques of this disclosure to determine a composite estimate of a limit of autoregulation based on PRx values for use where one of sensing devices 150-152 includes an intracranial pressure (ICP) probe.

In the example of FIG. 9, processing circuitry 110 determines sets of values for a first physiological parameter and a second physiological parameter (900 and 902). For example, processing circuitry 110 may determine a set of MAP values and a set of oxygen saturation values based on two signals received by processing circuitry 110 (see, e.g., indicators 310 and 320 shown in the FIG. 3). Processing circuitry 110 determines a set of correlation coefficient values based on the values of the first and second physiological parameters (904).

In the example of FIG. 9, processing circuitry 110 determines a metric of the correlation coefficient values for each bin of two or more pluralities of bins (906A and 906B). Processing circuitry 110 then determines individual estimates of a limit of autoregulation for each of the two or more pluralities of bins (908A and 908B). Processing circuitry 110 determines a composite estimate of the limit of autoregulation based on the individual estimates determined from each plurality of bins (910). The composite estimate may be a mean of the individual estimates or a weighted average of the individual estimates, where processing circuitry can determine the weighting of each individual estimate based on the width and/or separation distance of the corresponding plurality of bins.

In the example of FIG. 9, processing circuitry 110 determines an autoregulation status of the patient based on the composite estimate of the limit of autoregulation (912). Processing circuitry 110 may optionally determine a confidence measure based on the individual estimates (914), and processing circuitry 110 may use the confidence measure to determine the autoregulation status. Processing circuitry 110 may determine the confidence measure based on the difference between the individual estimates and/or on the difference between the individual estimates and a previous composite estimate. The confidence measure may indicate a measure of the reliability of the individual estimates and the current composite estimate.

In response to determining that there is a relatively large difference between the individual estimates, processing circuitry 110 may determine a confidence measure indicating relatively low reliability for the current composite measure. In response to determining that a confidence measure indicating relatively low reliability, processing circuitry 110 may weight the current composite estimate less heavily, causing a previous composite measure to have a higher weighting. In some examples, processing circuitry 110 determines a final estimate of the limit of autoregulation based on a weighted average of the current composite estimate and the previous iteration of the final estimate of the limit of autoregulation. Processing circuitry 110 can assign a lower weighting factor to the current composite estimate based on determining a confidence measure that indicates that the current composite estimate is less reliable. Processing circuitry 110 can determine the weighting factor for the composite estimate such that the composite estimate is weighted higher when the first estimate is equal to the second estimate, as compared to when the first estimate is not equal to the second estimate. In this way, processing circuitry 110 can determine the autoregulation status by determining a confidence measure for the individual estimates and then determining a weighting factor for the composite estimate of the limit of autoregulation based on the confidence measure. Processing circuitry then outputs, for display via display 132, an indication of the composite estimate of the limit of autoregulation and/or an indication of the autoregulation status (916).

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to devices 100 and 200, processing circuitry 110, 210, 214, and 216, memories 120 and 220, displays 132 and 232, sensing circuitries 140-142, circuitries 240 and 245, sensing devices 150-152 and 250, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

As used herein, the term "circuitry" refers to an ASIC, an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. For example, any of the techniques or processes described herein may be performed within one device or at least partially distributed amongst two or more devices, such as between devices 100 and 200, processing circuitry 110, 210, 214, and 216, memories 120 and 220, sensing circuitries 140-142, and/or circuitries 240 and 245. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Elements of devices and circuitry described herein, including, but not limited to, devices 100 and 200, processing circuitry 110, 210, 214, and 216, memories 120 and 220, displays 132 and 232, sensing circuitries 140-142, circuitries 240 and 245, sensing devices 150-152 and 250 may be programmed with various forms of software. The one or more processors may be implemented at least in part as, or include, one or more executable applications, application modules, libraries, classes, methods, objects, routines, subroutines, firmware, and/or embedded code, for example.

Where processing circuitry 110 is described herein as determining that a value is less than or equal to another value, this description may also include processing circuitry 110 determining that a value is only less than the other value. Similarly, where processing circuitry 110 is described herein as determining that a value is less than another value, this description may also include processing circuitry 110 determining that a value is less than or equal to the other value. The same properties may also apply to the terms "greater than" and "greater than or equal to."

Various examples of the disclosure have been described. Any combination of the described systems, operations, or functions is contemplated. These and other examples are within the scope of the following claims.

What is claimed is:

1. A device comprising:
a display; and
processing circuitry configured to:
receive a first signal indicative of a first physiological parameter of a patient;
receive a second signal indicative of a second physiological parameter of the patient;
determine a set of correlation coefficient values that correlate values from a set of values of the first physiological parameter to values from a set of values of the second physiological parameter;
determine a metric of the correlation coefficient values for each bin of a first plurality of bins, wherein each bin of the first plurality of bins has a first bin parameter defined in terms of the first physiological parameter;
determine the metric of the correlation coefficient values for each bin of a second plurality of bins, wherein each bin of the second plurality of bins has a second bin parameter defined in terms of the first physiological parameter, the second bin parameter being different than the first bin parameter;
determine a composite estimate of a limit of autoregulation of the patient based on the metric of the correlation coefficient values for the first plurality of bins and the metric of the correlation coefficient values for the second plurality of bins;
determine an autoregulation status of the patient based on the composite estimate of the limit of autoregulation; and
output, for display via the display, an indication of the autoregulation status.

2. The device of claim 1, wherein the processing circuitry is configured to determine the composite estimate of the limit of autoregulation at least in part by:
determining a first estimate of the limit of autoregulation based on the metric of the correlation coefficient values for the first plurality of bins;
determining a second estimate of the limit of autoregulation based on the metric of the correlation coefficient values for the second plurality of bins; and
determining the composite estimate of the limit of autoregulation based on the first estimate of the limit of autoregulation and the second estimate of the limit of autoregulation.

3. The device of claim 2, wherein the processing circuitry is configured to determine the composite estimate at least in part by determining an average of the first estimate of the limit of autoregulation and the second estimate of the limit of autoregulation.

4. The device of claim 2,
wherein the processing circuitry is configured to determine the composite estimate of the limit of autoregulation at least in part by determining a confidence measure for the first estimate of the limit of autoregulation and the second estimate of the limit of autoregulation, and
wherein the processing circuitry is configured to determine the autoregulation status at least in part by determining a weighting factor for the composite estimate of the limit of autoregulation based on the confidence measure.

5. The device of claim 4, wherein the processing circuitry is configured to determine the weighting factor such that the composite estimate is weighted higher in a first instance when the first estimate is equal to the second estimate than in a second instance when the first estimate is not equal to the second estimate.

6. The device of claim 2, wherein the limit of autoregulation is a lower limit of autoregulation, and wherein the processing circuitry is configured to determine the composite estimate of the lower limit of autoregulation at least in part by determining a lowest value of the first physiological parameter at which the metric of the correlation coefficient values is less than a threshold level.

7. The device of claim 1,
wherein the first bin parameter comprises a first width,
wherein the second bin parameter comprises a second width,
wherein each width of the first width and the second width is defined by a difference of a respective minimum value of the first physiological parameter and a respective maximum value of the first physiological parameter, and
wherein the processing circuitry is configured to determine the metric of the correlation coefficient values at least in part by determining the metric of the correlation coefficient values associated with values of the first physiological parameter in a range of greater than the respective minimum value and less than the respective maximum value.

8. The device of claim 1, wherein the metric of the correlation coefficient values comprises a median of the correlation coefficient values within the respective bin of the set of bins.

9. The device of claim 1, wherein the metric of the correlation coefficient values comprises a mean of the correlation coefficient values within the respective bin of the set of bins.

10. The device of claim 1,
wherein the first bin parameter comprises a first width,
wherein the second bin parameter comprises a second width, and
wherein at least one of the first width or the second width is less than or equal to four millimeters of mercury (mmHg).

11. The device of claim 10, wherein at least one of the first width or the second width is in a range of greater than or equal to one mmHg and less than or equal to three mmHg.

12. The device of claim 1,
wherein the first bin parameter comprises a first distance by which a center of each bin of the first plurality of bins is offset from a center of an adjacent bin of the first plurality of bins, and
wherein the second bin parameter comprises a second distance by which a center of each bin of the second plurality of bins is offset from a center of an adjacent bin of the second plurality of bins, the second distance being different than the first distance.

13. The device of claim 12, wherein at least one of the first distance or the second distance is less than or equal to four millimeters of mercury mmHg.

14. The device of claim 12, wherein at least one of the first distance or the second distance is in a range of greater than or equal to one millimeters of mercury (mmHg) and less than or equal to three mmHg.

15. The device of claim 1, wherein the processing circuitry is configured to determine the metric of the correlation coefficient values for each respective bin of the first plurality of bins at least in part by:
determining a first mean and a standard deviation of the correlation coefficient values for the respective bin;

determining an outlier correlation coefficient that is greater than three times the standard deviation from the first mean; and determining a second mean of the correlation coefficient values, excluding the outlier correlation coefficient, for the respective bin.

16. A method comprising:

receiving, by processing circuitry of a device and from sensing circuitry of the device, a first signal indicative of a first physiological parameter of a patient;

receiving, by the processing circuitry and from the sensing circuitry, a second signal indicative of a second physiological parameter of the patient;

determining, by the processing circuitry, a set of correlation coefficient values that correlate values from a set of values of the first physiological parameter to values from a set of values of the second physiological parameter;

determining, by the processing circuitry, a metric of the correlation coefficient values for each bin of a first plurality of bins, wherein each bin of the first plurality of bins has a first bin parameter defined in terms of the first physiological parameter;

determining, by the processing circuitry, a metric of the correlation coefficient values for each bin of a second plurality of bins, wherein each bin of the second plurality of bins has a second bin parameter defined in terms of the first physiological parameter, the second bin parameter being different than the first bin parameter;

determining, by the processing circuitry, a composite estimate of a limit of autoregulation of the patient based on the metric of the correlation coefficient values for the first plurality of bins and the metric of the correlation coefficient values for the second plurality of bins;

determining, by the processing circuitry, an autoregulation status of the patient based on the composite estimate of the limit of autoregulation; and outputting, by the processing circuitry for display, an indication of the autoregulation status.

17. A device comprising:

a display; and processing circuitry configured to:

receive a first signal indicative of a first physiological parameter of a patient;

receive a second signal indicative of a second physiological parameter of the patient;

determine a set of correlation coefficient values that correlate values from a set of values of the first physiological parameter to values from a set of values of the second physiological parameter;

determine a metric of the correlation coefficient values for each bin of a first plurality of bins at least in part by determining a first weighting factor for each correlation coefficient, wherein each bin of the first plurality of bins has a first bin parameter defined in terms of the first physiological parameter;

determine the metric of the correlation coefficient values for each bin of a second plurality of bins at least in part by determining a second weighting factor for each correlation coefficient, wherein each bin of the second plurality of bins has a second bin parameter defined in terms of the first physiological parameter, the second bin parameter being different than the first bin parameter;

determine a composite estimate of a limit of autoregulation of the patient based on the metric of the correlation coefficient values for the first plurality of bins and the metric of the correlation coefficient values for the second plurality of bins;

determine an autoregulation status of the patient based on the composite estimate of the limit of autoregulation; and output, for display via the display, an indication of the autoregulation status.

18. The device of claim 17, wherein the processing circuitry is configured to determine the first weighting factor based on an age of each correlation coefficient within the respective bin such that more recent correlation coefficient values are weighted higher than less recent correlation coefficient values, and wherein the processing circuitry is configured to determine the second weighting factor based on the age of each correlation coefficient within the respective bin such that more recent correlation coefficient values are weighted higher than less recent correlation coefficient values.

19. The device of claim 17, wherein the processing circuitry is configured to determine the first weighting factor based on a distance between a center of a bin of the first plurality of bins and a value of the first physiological parameter associated with the respective correlation coefficient such that correlation coefficient values closer to the center of the bin are weighted higher than correlation coefficient values farther from the center of the bin, and wherein the processing circuitry is configured to determine the second weighting factor based on a distance between a center of a bin of the second plurality of bins and the value of the first physiological parameter associated with the respective correlation coefficient such that correlation coefficient values closer to the center of the bin are weighted higher than correlation coefficient values farther from the center of the bin.

20. The device of claim 17, wherein the processing circuitry is configured to determine the first weighting factor based on a signal quality metric, and wherein the processing circuitry is configured to determine the second weighting factor based on the signal quality metric.

* * * * *